(12) United States Patent
Qian et al.

(10) Patent No.: US 7,655,665 B2
(45) Date of Patent: Feb. 2, 2010

(54) NITROMETHYLENE DERIVATIVES AND THEIR USE

(75) Inventors: Xuhong Qian, Shanghai (CN); Zhong Li, Shanghai (CN); Zhongzhen Tian, Shanghai (CN); Qingchun Huang, Shanghai (CN); Jichao Fang, Shanghai (CN); Gonghua Song, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 11/751,836

(22) Filed: May 22, 2007

(65) Prior Publication Data

US 2007/0281950 A1 Dec. 6, 2007

Related U.S. Application Data

(63) Continuation of application No. PCT/CN2005/000617, filed on Apr. 30, 2005.

(30) Foreign Application Priority Data

Nov. 23, 2004 (CN) .................. 200410084457.1

(51) Int. Cl.
  *A01N 43/90* (2006.01)
  *A01N 43/42* (2006.01)
  *C07D 487/04* (2006.01)
  *C07D 491/02* (2006.01)

(52) U.S. Cl. ................ 514/259.1; 514/300; 544/281; 546/121

(58) Field of Classification Search ................ 546/121, 546/122; 514/300, 259.1; 544/281
See application file for complete search history.

(56) References Cited

U.S. PATENT DOCUMENTS

| | | | |
|---|---|---|---|
| 4,914,113 A | | 4/1990 | Shiokawa et al. |
| 4,960,780 A | * | 10/1990 | Shiokawa et al. ........... 514/300 |
| 5,614,527 A | | 3/1997 | Kinoshita et al. |

FOREIGN PATENT DOCUMENTS

| | | |
|---|---|---|
| EP | 0 386 565 | 9/1990 |
| JP | 8-259568 | 10/1996 |
| JP | 8-291171 | 11/1996 |
| WO | WO 9519977 | 7/1995 |

* cited by examiner

*Primary Examiner*—D. Margaret Seaman
*Assistant Examiner*—Niloofar Rahmani
(74) *Attorney, Agent, or Firm*—Hamre, Schumann, Mueller & Larson, P.C.

(57) ABSTRACT

The present invention discloses nitromethylene derivatives and the uses thereof. These derivatives are obtained by adding ring structure onto the known nitromethylene compounds, by which both their stability for light and their liposolubility are increased. Furthermore, by using the substituents linked to ether bond, the steric orientation of the nitro group and the liposolubility of the compounds are controlled. The insecticidal activity tests show that the compounds and their derivatives of the invention display high efficiency on killing various destructive insects with piercing-sucking type or scratching type mouthparts, such as aphid, leafhopper, plant hopper, thrips and white fly.

10 Claims, No Drawings

NITROMETHYLENE DERIVATIVES AND THEIR USE

CROSS-REFERENCE TO RELATED APPLICATIONS

This application is a continuation of International application number PCT/CN2005/000617, filed Apr. 30, 2005 which claims priority to Chinese application No. CN 200410084457.1 filed Nov. 23, 2004, the contents of both are herein incorporated in their entirety by reference.

FIELD OF THE INVENTION

This invention relates to nitromethylene derivatives and the uses thereof.

BACKGROUND OF THE INVENTION

Alkaloid nicotine is a natural insecticide from the extraction of tobacco leaves, and it acts on the postsynaptic nicotinic acetylcholine receptor (nAchRs). By so far, using natural nicotine as a leading compound, researchers have been making efforts to look for and develop a new insecticidally active compound having a similar structure and the same mechanism of action as nicotine. Since Soloway et al firstly reported the insecticidally active nitromethylene heterocyclic compounds in 1978, researchers have been changing the functional groups of nitromethylene heterocyclic compounds and Bayer AG successfully developed the first nicotine insecticide—Imidacloprid in middle 1980 s. Due to its unique mechanism of action, no mutual resistance with common insecticides, high effect, broad spectrum, good root systemic ability, contact toxicity, stomach toxicity, low toxicity to mammalian, and safety to the environment, this kind of nicotine insecticide catches people's attention at once. A series of nicotine insecticide such as Thiacloprid, Clothianidin, Thiamethoxam, Acetamiprid, Nitenpyram and Dinotefuran are developed (EP 247477, 296453, 685477, 235725, 235725, 315826, 192060, 244777, 0386565, 580553, 1031566, JP 62292765, 8259568, 8291171, 7242633).

Compared to Imidacloprid, nitromethylene compounds have higher binding affinity and insecticidal activity. Whereas its use as an insecticide has been restricted by its instability to light and low LogP value. Therefore, the technical problem to be solved by the present invention is how to structurally modify the highly active nitromethylene compound to make it useful as an insecticide.

SUMMARY OF THE INVENTION

The object of this invention is to provide a kind of nitromethylene derivatives and the uses thereof.

Based on the current nitromethylene compound, this invention adds a new ring to its structure in order to enhance its light stability and liposolubility. Furthermore, this invention can control the space orientation and liposolubility by the substituent linked to an ether bond.

According to the first aspect of this invention, it is provided a nitromethylene derivative of formula (I), or an agriculturally acceptable salt thereof.

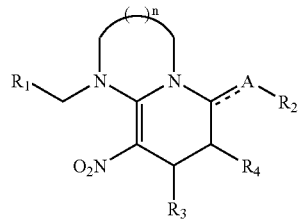

(I)

wherein $R_1$ is a substituted or unsubstituted 5- or 6-membered heterocycle containing nitrogen, oxygen and/or sulfur, the substituents are one to three substituents selected from the group consisting of a halogen atom, $C_{1-4}$ haloalkyl and $C_{1-4}$ haloalkoxyl;

$R_2$ is a hydrogen atom, a saturated or unsaturated $C_{1-8}$ hydrocarbyl group, a saturated or unsaturated $C_{1-8}$ halogenated hydrocarbyl group, —$CH_2CH_2OCH_2CH_3$, —$CH_2CH_2OCH_3$, a substituted or unsubstituted phenyl group, a substituted or unsubstituted benzyl group, a substituted or unsubstituted $C_{1-8}$ alkoxyl group which may be saturated or unsaturated, wherein the substituents are one to three substituents selected from the group consisting of a halogen atom, $C_{1-4}$ haloalkyl and $C_{1-4}$ haloalkoxyl;

or $R_2$ is a group of the following formula:

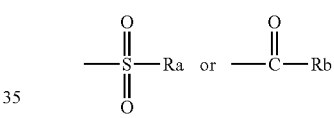

wherein Ra is methyl, trifluoromethyl or phenyl; Rb is methyl, trifluoromethyl, pyridyl, phenyl or phenyl substituted by a halogen atom and/or a nitro group;

$R_3$ and $R_4$ independently is hydrogen, a substituted or unsubstituted $C_{1-3}$ alkyl group, wherein the substituents are one to three substituents selected from the group consisting of halogen, $C_{1-4}$ haloalkyl and $C_{1-4}$ haloalkoxyl;

A is O, S or N;

n is 0 or 1.

Preferably, $R_1$ is one of pyridyl, thiazolyl, pyrimidinyl, tetrahydrofuryl, oxazolyl, or halide thereof (especially chloride); $R_2$ is saturated or unsaturated $C_{1-8}$ hydrocarbyl, saturated or unsaturated $C_{1-8}$ halogenated hydrocarbyl, —$CH_2CH_2OCH_2CH_3$, —$CH_2CH_2OCH_3$, a saturated or unsaturated $C_{1-8}$ alkoxyl group; $R_3$ is hydrogen or methyl; $R_4$ is hydrogen or $C_{1-3}$ alkyl group.

One kind of especially preferable compound has the structure of formula II (i.e. $R_3=R_4=H$, n=0):

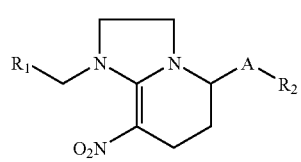

(II)

wherein $R_1$, $R_2$ and A are defined as above.

More preferably, $R_1$ represents

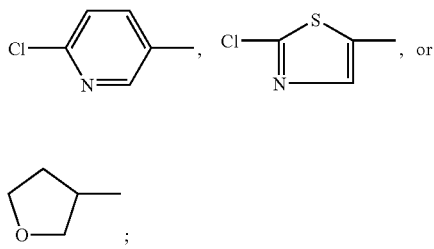

More preferably, $R_2$ is saturated or unsaturated $C_{1-5}$ hydrocarbyl group, a saturated or unsaturated $C_{1-5}$ hydrocarbyl group which may be substituted by halogen (such as fluorine or chlorine), —$CH_2CH_2OCH_2CH_3$, —$CH_2CH_2OCH_3$, saturated or unsaturated $C_{1-8}$ alkoxyl group.

More preferably, A is O or S.

According to the second aspect of this invention, it is provided the use of the nitromethylene derivatives or the salts thereof to prepare chemical insecticide for agriculture.

According to the third aspect of this invention, it is provided an insecticidal composition comprising an effective amount of the compound of the present invention or an agriculturally acceptable salt thereof in mixture with an agriculturally acceptable carrier or diluent.

The nitromethylene derivatives can be synthesized by the following scheme:

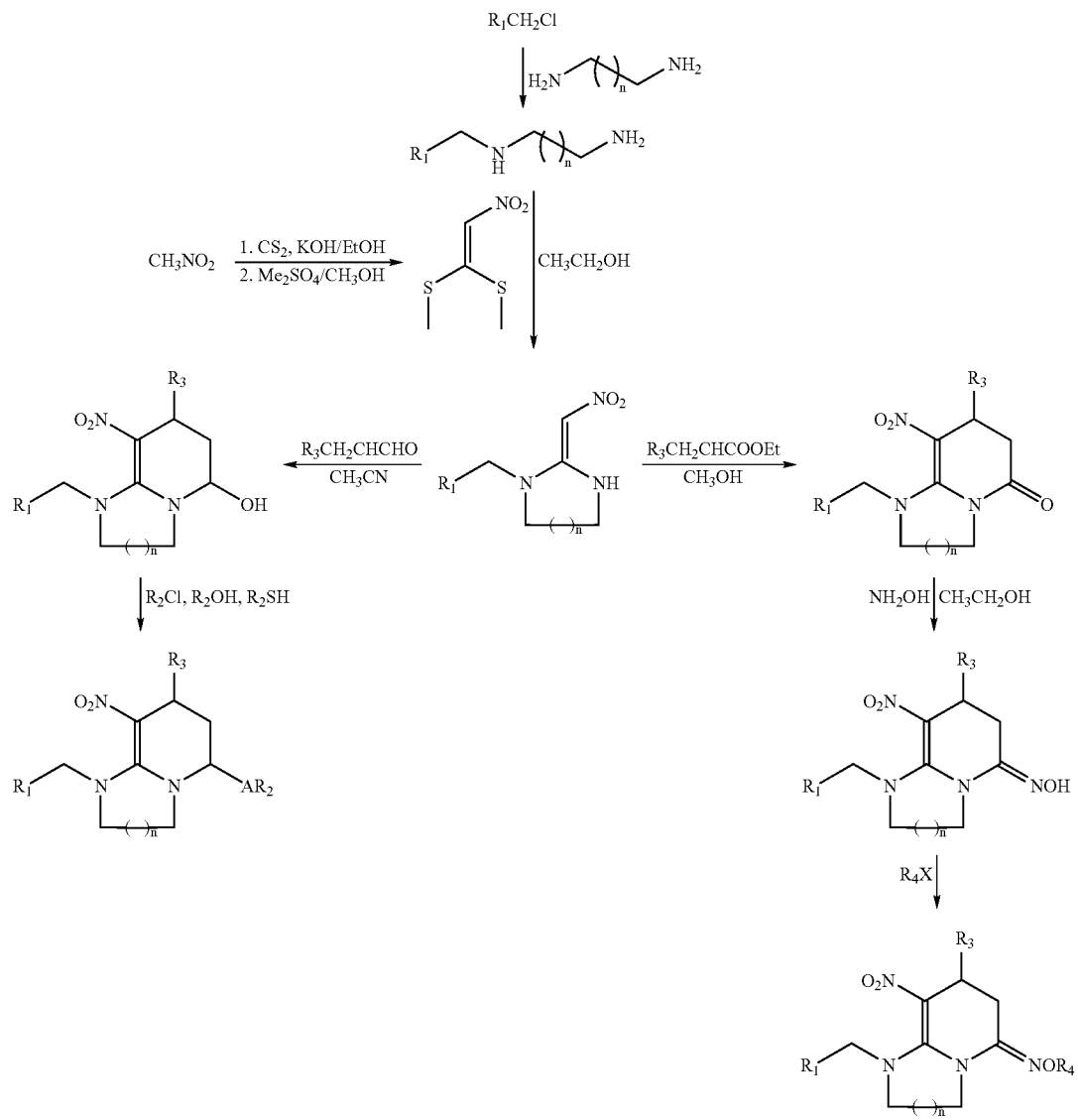

n = 0 or 1

In one of the preferable example, the ether derivatives containing a nitromethylene structure can be prepared by the following steps:

(1): A mixture of nitromethane and carbon bisulfide dissolved in alcohols is added dropwise to the solution of potassium hydroxide in alcohol at room temperature. The reaction is carried out at the temperature range of 0-35° C. for 2-10 hours. The solid is filtered out to afford a crude product potassium 2-nitroethene-1,1-bis(thiolate) which is a brown yellow powder.

(2): Potassium 2-nitroethene-1,1-bis(thiolate) is dissolved in alcohol, and then to the resulting mixture is added dropwise dimethyl sulfate solution. The reaction is stirred at room temperature for 2-8 hours. The mixture is filtrated to obtain crude product 1,1-dimethylthio-2-nitroethene, which is a light brown yellow powder.

(3): The solution of 2-chloro-5-(chloromethyl)pyridine in acetonitrile is added dropwise to 5-10 mole of diamine solution. The reaction is carried out at the temperature range of 0-50° C. for 5-10 hours. The mixture is distillated under reduced pressure to remove diamine, and then dissolved in ethyl acetate and evaporated to obtain $N^1$-((6-chloropyridin-3-yl)methyl)diamine (4): The mixture of $N^1$-((6-chloropyridin-3-yl)methyl) diamine and 1,1-dimethylthio-2-nitroethene is dissolved in ethanol and refluxed for 4-8 hours to obtain the product nitromethylene compound.

(5): In the presence of a acid catalyst such as hydrochloric acid, sulfuric acid, acetic acid, trifluoroacetic acid and the like, nitromethylene compound reacts with acraldehyde to obtain a new nitromethylene compound having hydroxyl.

In the presence of a catalytic amount of acid catalyst such as hydrochloric acid, sulfuiric acid, acetic acid, trifluoroacetic acid and the like, the mixture of the new nitromethylene compound having hydroxyl and various alcohols is refluxed to obtain the target compound.

In the presence of a catalytic amount of acid catalyst such as Lewis acid, such as trifluoroboric acid, aluminum trichloride, and the like, the mixture of the new nitromethylene compound having a hydroxyl and various mercaptans is refluxed to obtain the target compound.

In the presence of an acid-binding agent such as organic or inorganic alkali, for example pyridine, triethylamine, potassium carbonate, potassium hydroxide and the like, the mixture of the new nitromethylene compound having hydroxyl and various acyl chlorides is refluxed to obtain the target compound.

In another preferable example, the Schiff's base derivatives of nitromethylene compound can be prepared by the following steps:

(1) The mixture of nitromethylene compound and methyl acrylate reacts at 0-100° C. to obtain a new nitromethylene compound bearing carbonyl group;

(2) The mixture of the new nitromethylene compound with carbonyl group and hydroxylamine is refluxed to obtain new Schiffs base derivatives of nitromethylene compound The Schiff's base derivatives of nitromethylene compound can react with halogen substituted alkanes to obtain the target compound in the presence of organic or inorganic alkali such as sodium hydride, sodium methoxide, sodium ethoxide, potassium hydroxide and the like.

The Schiff's base derivatives of nitromethylene compound can react with various acyl chlorides to obtain the target compound in the presence of an acid-binding agent such as organic or inorganic alkali, for example pyridine, triethylamine, potassium carbonate, and the like.

The invention is further illustrated by the following examples. It should be appreciated that these examples are only intended to illustrate the invention, but not to limit the scope of the invention. For the experimental methods in the following examples, they are performed under routine conditions, or as instructed by the manufacturers, unless otherwise specified.

EXAMPLE 1

Synthesis of 1-((6-chloropyridin-3-yl)methyl)-8-nitro-1,2,3,5,6,7-hexahydro imidazo[1,2-a]pyridin-5-ol (compound 1)

(1) Synthesis of potassium 2-nitro-ethene-1,1-bis(thiolate)

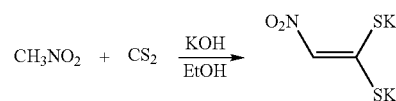

4 g (0.03 mol) of nitromethane and 6 ml (0.05 mol) of carbon bisulfide were placed in a 100 ml three-necked flask and 10 ml of ethanol was added as a solvent, and then the solution was stirred. To the resulting solution was added slowly and dropwise the solution of 8 g (0.14 mol) of potassium hydroxide in 40 ml of ethanol at room temperature over nearly 30 min. Since the reaction was exothermic, the rate of addition depended on the reaction temperature which was preferably between 30-35° C. After the addition was complete, the mixture was further stirred for 2 hours, filtered to obtain a crude product, which was a brown yellow powder in 72% yield.

(2): Synthesis of 1,1-dimethylthio-2-nitroethene

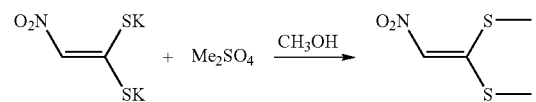

To a solution of 2 g (0.0094 mol) of potassium 2-nitroethene-1,1-bis(thiolate) in 10 ml of dried methanol, 0.0187 mol of dimethyl sulphate was added. The mixture was then stirred for 2 hours at room temperature. The precipitated solid was filtered to obtain crude product, which was a light brown yellow powder in 70% yield.

GC/ MS(m/s) 165 (31) M+,148(17), 104(66), 86(100), 72(93), 57(20).

(3): Synthesis of $N^1$-((6-chloropyridin-3-yl)methyl)ethane-1,2-diamine

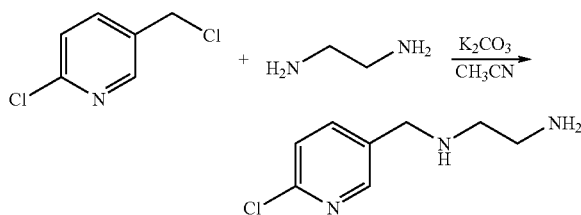

To a stirred solution of 4.2 g (0.03 mol) of potassium carbonate and 10 ml (0.15 mol) of ethylenediamine in a 50 ml of flask placed in an ice bath, 4.8 g (0.03 mol) of 2-chloro-5-

(chloromethyl)pyridine dissolved in 15 ml of acetonitrile was added dropwise and slowly for nearly 20 min. After addition, the ice bath was removed and then the mixture was stirred for 8 hours at room temperature. After the reaction was stopped, a large amount of water was added to dissolve potassium carbonate and ethylenediamine, and the mixture was extracted with dichlormethane. The lower organic phase was collected, dried, and evaporated to dryness (It was better to remove all of the ethylenediamine in the solvent since its presence would influence the following step). The obtained product was yellow oily liquid in 68% yield.

GC MS(m/s) 185 (5) M+, 155(49), 126(100), 99(9), 90(12).

(4): Synthesis of 2-chloro-5-((2-(nitromethylene)imidazo-lidin-1-yl)methyl) pyridine

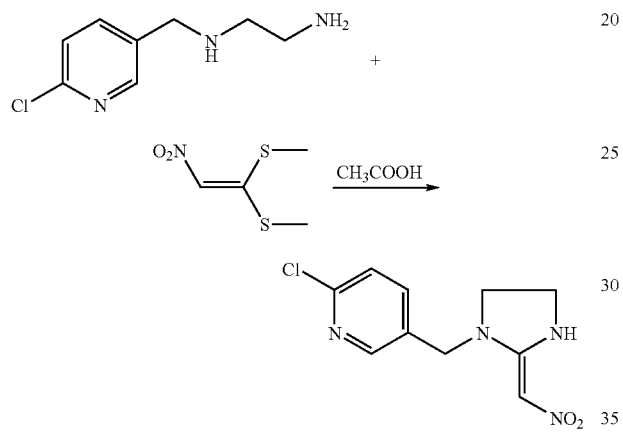

2.5 g (0.0178 mol) of 1,1-dimethylthio-2-nitroethene, 3.3 g (0.0178 mol) of $N^1$-((6-chloropyridin-3-yl)methyl)ethane-1, 2-diamine were added to 15 ml of ethanol. The resulting mixture was heated under reflux for 4 hours at 80-90° C. The mixture was then cooled to educe solid, concentrated, filtrated and dried to give a light yellow powder in 56% yield.

$R_f$=0.46 (petroleum ether: ethyl acetate=1:1). Mp=156.9° C.-161.8° C. GC MS (m/s) 220 (25), 126(100), 90(9).

(5): Synthesis of 1-((6-chloropyridin-3-yl)methyl)-8-nitro-1,2,3,5,6,7-hexahydro imidazo[1,2-a]pyridin-5-ol

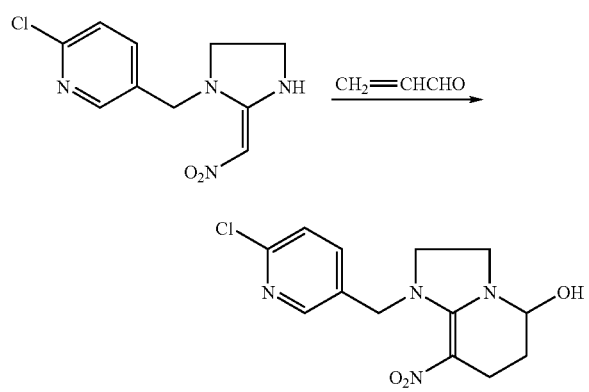

A mixture of 0.509 g (0.002 mol) of 2-chloro-5-((2-(nitromethylene)imidazolidin-1-yl)methyl)pyridine, 15 ml of anhydrous acetonitrile, 0.15 ml of acrylaldehyde and a catalytic amount of HCl place in a 50 ml of flask was heated to 40° C. and the mixture was kept at 40° C. and stirred for 12 hours. After the reaction was stopped, the precipitated solid was filtrated to give a crude product. After recrystallization, the pure product was a yellow powder in 40% yield.

Mp=169.0-172.1° C. IR (KBr, cm$^{-1}$) 3190, 1560, 1520, 1370, 1300, 1150, 970, 590. $^1$HNMR (CDCl$_3$), δ (ppm)500 MHz: 8.37(d, J=2 Hz, 1H, Py-H), 7.85(dd, $J_1$=2 Hz, $J_2$=8.29 Hz, 1H, Py-H), 7.41(d, J=8 Hz, 1H, Py-H), 6.33(d, J=5.47 Hz, 1H, —OH), 4.86(m, 1H, —CHOH), 4.65(dd, $J_1$=$J_2$=15 Hz, 2H, —CH$_2$—N—), 3.52(m, 4H, imidazolidine-H), 2.60(m, 2H, —CH$_2$CH$_2$—), 1.79(m, 2H, —CH$_2$CH$_2$—). GC MS (m/s) 220 (25), 126(100), 90(9). Elementary analysis Calculated: C, 50.25; H, 4.87; N, 18.03; found C, 50.12; H, 4.82; N, 18.31.

EXAMPLE 2

Synthesis of 1-((6-chloropyridin-3-yl)methyl)-5-methoxy-8-nitro-1,2,3,5,6,7-hexahydroimidazo[1,2-a]pyridine (compound 2)

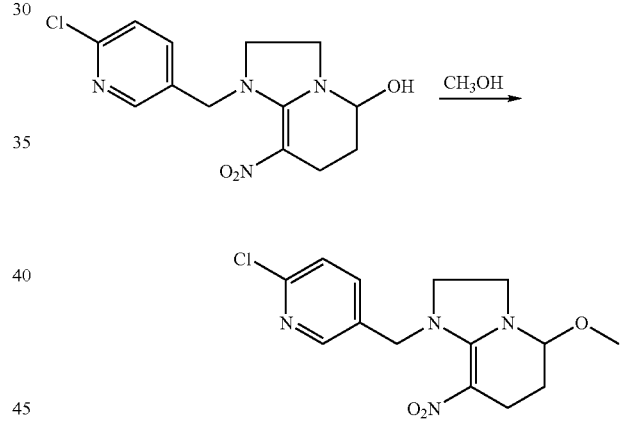

0.31 g (0.0001 mol) of compound 1 was added to a 50 ml of round-bottomed flask, and 15 ml of methanol and a catalytic amount of glacial acetic acid were added. The resulting mixture was refluxed and followed by TLC. After the reaction was stopped, the solvent was removed. The residue was then separated to give a pure yellow powder by column chromatography in 90% yield.

Mp=154.0-155.4° C. IR (KBr, cm$^{-1}$) 2900, 1560, 1350, 1080, 900, 760, 590 $^1$H NMR (CDCl$_3$), δ (ppm) 500 MHz: 8.32(d, J=2 Hz, 1H, Py-H), 7.88(dd, $J_1$=2 Hz, $J_2$=8 Hz, 1H, Py-H), 7.35(d, J=8 Hz, 1H, Py-H), 4.78(d, $J_1$=15 Hz, $J_2$=15 Hz, 2—CH$_2$—N—), 4.48(t, $J_1$=3 Hz, $J_2$=3 Hz, 1H, —CHO—), 3.60(m, 4H, imidazolidine-H), 3.19(m, 3H, —OCH$_3$), 2.90(m, 2H, —CH$_2$CH$_2$—), 1.95(m, 2H, —CH$_2$CH$_2$—) Elementary analysis Calculated: C, 51.78; H 5.28; N, 17.25; found C, 51.95; H, 5.12; N, 17.04.

EXAMPLE 3

Synthesis of 1-((6-chloropyridin-3-yl)methyl)-5-ethoxy-8-nitro-1,2,3,5,6,7-hexahydroimidazo[1,2-a]pyridine(compound 3)

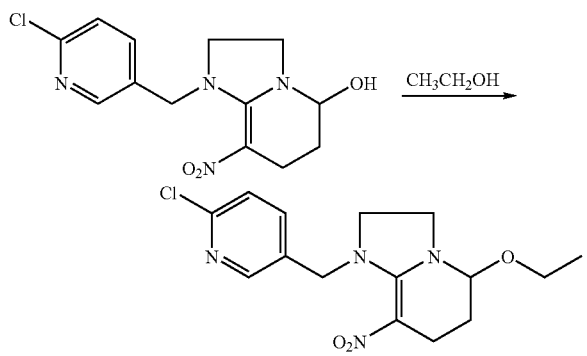

Following the steps described in example 2, except that ethanol was used instead of methanol, a pure yellow powder was obtained by column chromatography in 85% yield.

Mp=126.4-128.1° C. IR (KBr) 3050 m, 2870 m, 1570 vs, 1500 s, 1310 vs, 1150 vs, 1030 s, 970 m, 760 m, 580 m cm$^{-1}$ $^1$H NMR (CDCl$_3$) δ (ppm) 500 MHz=8.33(d, J=2 Hz, 1H, Py-H), 7.91(dd, J$_1$=2 Hz, J$_2$=2 Hz, 1H, Py-H), 7.33(d, J=8 Hz, 1H, Py-H), 4.78(d, J$_1$=15 Hz, J$_2$=15 Hz, 2H, —CH$_2$—N—), 4.54(t, J$_1$=3 Hz, J$_2$=3 Hz, 1H, —CHO—), 3.68(m, 2H, —O—CH$_2$—), 3.57(m, 4H, imidazolidine-H), 2.87 (m, 2H, —CH$_2$CH$_2$—), 1.89(m, 2H, —CH$_2$CH$_2$—), 1.23(t, J$_1$=7 Hz, J$_2$=7 Hz, 3H, —CH$_3$) Elementary analysis Calculated: C, 53.18; H, 5.65; N, 17.54; found C, 53.64,; H, 5.57; N, 17.68.

EXAMPLE 4

Synthesis 1-((6-chloropyridin-3-yl)methyl)-5-propoxy-8-nitro-1,2,3,5,6,7-hexahydroimidazo[1,2-a]pyridine (compound 4)

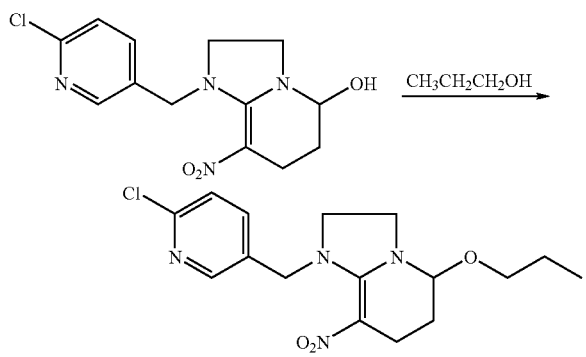

Following the steps described in example 2, except that propanol was used instead of methanol, a pure yellow powder was obtained by column chromatography in 78% yield.

Mp=115.71-117.6° C. IR (KBr cm$^{-1}$) 2900, 2370, 1580, 1500, 1310, 1150, 1090, 1000, 820 $^1$H NMR (CDCl$_3$) δ (ppm) 500 MHz: 8.37(d, J=2 Hz, 1H, Py-H), 7.89(dd, J$_1$=2 Hz, J$_2$=2 Hz, 1H, Py-H), 7.32(d, J=8 Hz, 1H, Py-H), 4.77(d, J$_1$=15 Hz, J$_2$=15 Hz, 2H, —CH$_2$—N—), 4.56(t, J$_1$=3 Hz, J$_2$=3 Hz, 1H, —CHO—), 3.68(m, 2H, —O—CH$_2$—), 3.57(m, 4H, imidazolidine-H), 2.84 (m, 2H, —CH$_2$CH$_2$—), 1.89(m, 2H, —CH$_2$CH$_2$—), 1.68(m, 2H, —CH$_2$CH$_3$), 0.93(t, 3H, —CH$_3$) Elementary analysis Calculated: C, 54.47; H, 6.00; N, 15.88; found C, 54.62; H, 5.98; N, 15.54.

EXAMPLE 5

Synthesis of 1-((6-chloropyridin-3-yl)methyl)-5-isopropoxy-8-nitro-1,2,3,5,6,7-hexahydroimidazo[1,2-a]pyridine (compound 5)

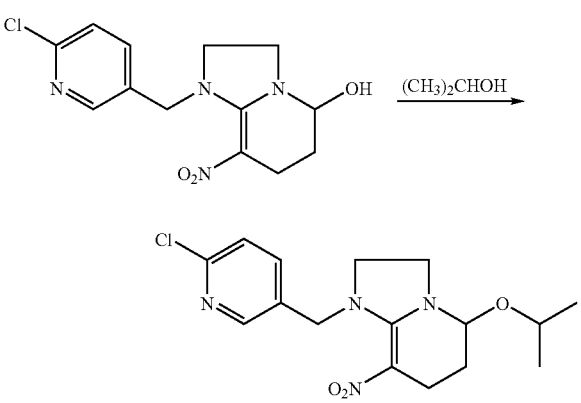

Following the steps described in example 2, except that propan-2-ol was used instead of methanol, a pure yellow powder was obtained by column chromatography in 80% yield.

Mp=129.9-134.6 ° C. IR (KBr cm$^{-1}$) 2900, 2370, 1560, 1330, 1200, 1120, 1070, 1000, 970, 820, 590 $^1$H NMR (CDCl$_3$) δ (ppm) 500 MHz: 8.32(d, J=2 Hz, 1H, Py-H), 7.91(dd, J$_1$=2 Hz, J$_2$=2 Hz, 1H, Py-H), 7.31(d, J=8 Hz, 1H, Py-H), 4.76(d, J$_1$=15 Hz, J$_2$=15 Hz, 2H, —CH$_2$—N—), 4.59 (t, J$_1$=3 Hz, J$_2$=3 Hz, 1H, —CHO—), 3.72 (m, 2H, —O—CH—), 3.69(m, 4H, imidazolidine-H), 2.89(m, 2H, —CH$_2$CH2—), 1.87(m, 2H, —CH$_2$CH$_2$—), 1.21(m, 6H, —(CH$_3$)$_2$) Elementary analysis Calculated: C, 54.47; H, 6.00; N, 15.88; found C, 54.52; H, 5.84; N, 15.90.

EXAMPLE 6

Synthesis of 1-((6-chloropyridin-3-yl)methyl)-8-nitro-5-pentyloxy-1,2,3,5,6,7-hexahydroimidazo[1,2-a]pyridine (compound 6)

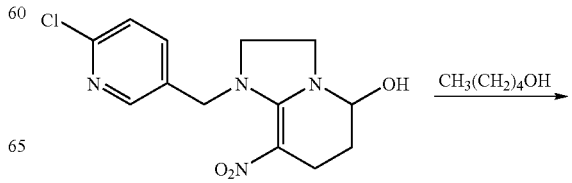

-continued

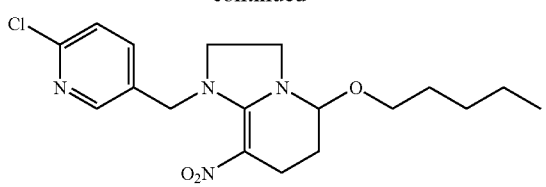

Following the steps described in example 2, except that pentanol was used instead of methanol, a pure yellow powder was obtained by column chromatography in 75% yield.

Mp=83.5-85.2° C. IR (KBr cm$^{-1}$)2900, 2720, 1670, 1550, 1440, 1330, 1150, 1080, 980, 810, 750, 590 $^1$H NMR (CDCl$_3$) δ (ppm) 500 MHz : 8.33(d, J=2 Hz, 1H, Py-H), 7.92(dd, J$_1$=2 Hz, J$_2$=8 Hz, 1H, Py-H), 7.31(d J=8 Hz, 1H, Py-H), 4.77(d, J$_1$=15 Hz, J$_2$=15 Hz, 2H, —CH2—N—), 4.59 (s, 1H, —CHO—), 3.68(m, 2H, —O—CH2—), 3.51(m, 4H, imidazolidine-H), 2.86(m, 2H, —CH2CH2—), 1.95(m, 2H, —CH2CH2—), 1.58(m, 2H, —O—(CH2)3—), 1.32(m, 4H, —O—(CH2)3—), 0.92(t, 3H, —CH3) Elementary analysis Calculated: C, 57.76; H, 6.62; N, 14.71; found C, 57.68; H, 6.45; N, 14.42.

EXAMPLE 7

Synthesis of 5-(2-chloroethoxy)-1-((6-chloropyridin-3-yl)methyl)-8-nitro-1,2,3,5,6,7-hexahydroimidazo[1,2-a]pyridine (compound 7)

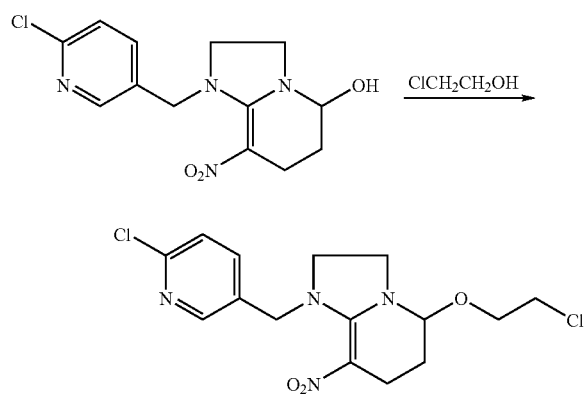

Following the steps described in example 2, except that 2-chloroethanol was used instead of methanol, a pure yellow powder was obtained by column chromatography in 79% yield.

Mp=158.5-159.4° C. IR (KBr cm$^{-1}$) 3000, 2370, 1560 s, 1350, 1280, 1130 $^1$H NMR (CDCl$_3$) δ (ppm) 500 MHz: 8.33(d, J=2 Hz, 1H, Py-H), 7.91(dd, J$_1$=2 Hz, J$_2$=8 Hz, 1H, Py-H), 7.32(t, J=8 Hz, 1H, Py-H), 4.75(d, J$_1$=15 Hz, J$_2$=15 Hz, 2H, —CH$_2$—N—), 4.66(t, J$_1$=3 Hz, J$_2$=3 Hz, 1H, —CHO—), 3.85(m, 4H, —O—(CH$_2$)$_2$—), 3.57(m, 4H, imidazolidine-H), 2.88 (m, 2H, —CH$_2$CH$_2$—), 1.93(m, 2H, —CH$_2$CH$_2$—) Elementary analysis Calculated: C, 48.27; H, 4.86; N, 15.01; found C, 48.47; H, 4.95; N, 14.40.

EXAMPLE 8

Synthesis of 1-((6-chloropyridin-3-yl)methyl)-9-nitro-2,3,4,6,7,8-hexahydro-1H-pyrido[1,2-a]pyrimidin-6-ol (compound 8)

(1): Synthesis of N$^1$-((6-chloropyridin-3-yl)methyl)propane-1,3-diamine

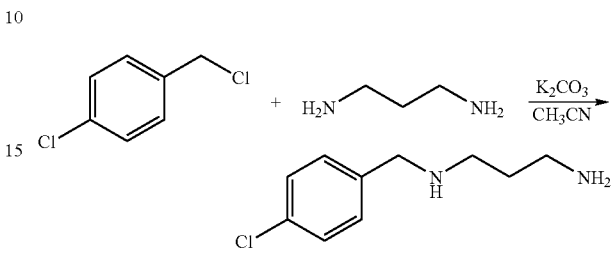

To a stirred solution of 2.07 g (0.015 mol) of potassium carbonate and 6.25 ml (0.075 mol) of propane-1,3-diamine in a 50 ml of flask placed in an ice bath, 2.42 g (0.015 mol) of 2-chloro-5-(chloromethyl)pyridine dissolved in 15 ml of acetonitrile was added dropwise and slowly for nearly 20 min. After addition, the ice bath was removed and then the mixture was stirred at room temperature for 8 hours. After the reaction was stopped, a large amount of water was added to dissolve potassium carbonate and propane-1,3-diamine, and the mixture was extracted with dichlormethane. The lower organic phase was collected, dried, and evaporated to dryness (It was better to remove all of the propane-1,3-diamine in the solvent since its presence would influence the following step). The obtained product was yellow oily liquid in 68% yield.

GC MS(m/s) 199 (5) M$^+$, 182(10), 167(12), 155(17), 141 (24), 126(100), 99(10), 90(13), 73(25), 56(10).

(2): Synthesis of 1-((6-chloropyridin-3-yl)methyl)-2-(nitromethylene)hexahydro pyrimidine

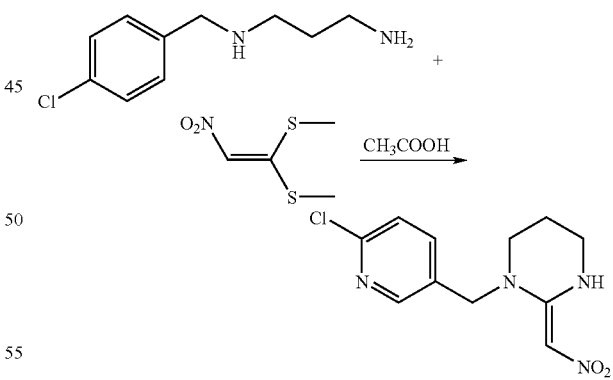

2.5 g (0.0178 mol) of 1,1-dimethylthio-2-nitroethene, 3.6 g (0.0178 mol) of N$^1$-((6-chloropyridin-3-yl)methyl)propane-1,3-diamine were added to 15 ml of ethanol. The resulting mixture was heated under reflux for 4 hours at 80-90 ° C. The mixture was then cooled to educe solid, concentrated, filtrated and dried to give light yellow powder in 56% yield.

R$_f$=0.19 (ethanol: dichlormethane =1:1) Mp=175.7° C.-182.6° C. GC MS (m/s) 225(100), 196(9), 154(10), 139 (11), 126(31), 113(10), 99(31)

(3): Synthesis of 1-((6-chloropyridin-3-yl)methyl)-9-nitro-2,3,4,6,7,8-hexahydro-1H-pyrido[1,2-a]pyrimidin-6-ol

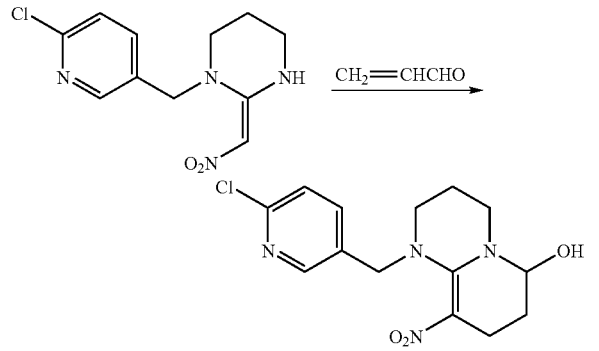

The preparation method was the same as that of example 1, except using 1-((6-chloropyridin-3-yl)methyl)-2-(nitromethylene)hexahydropyrimidine as a starting material. The reaction was stopped and the precipitated solid was filtrated to give a crude product, which was recrystallized to give the pure product in 51% yield.

Mp=172.7-173.9° C. IR (KBr, cm$^{-1}$) 2900, 2370, 1680, 1560, 1400, 1340, 1140, 980, 750, 590 $^1$HNMR (CDCl$_3$) δ (ppm) 500 MHz: 8.28(d, J=2 Hz, 1H, Py-H), 7.74(dd, J=2 Hz, J$_2$=2 Hz 1H, Py-H), 7.48(d, J=8 Hz, 1H, Py-H), 6.37(s, 1H, —OH), 4.82(s, 1H, —CHOC), 4.46(d, J$_1$=15 Hz, J$_2$=15 Hz, 2H, —CH$_2$—N—), 2.93(m, 4H, pyrimidine-H), 1.83(m, 2H, pyrimidine-H, 2H, —CH$_2$CH$_2$—), 1.07(m, 2H, —CH$_2$CH$_2$—). GC MS (m/s) 225(100), 196(9) 154(10), 139(11), 126(31), 113(10), 99(31) Elementary analysis Calculated: C, 51.78; H, 5.28; N, 17.25; found C, 52.92; H, 5.36; N, 17.11.

EXAMPLE 9

Synthesis of 1-((2-chlorothiazol-5-yl)methyl)-8-nitro-1,2,3,5,6,7-hexahydro imidazo[1,2-a]pyridin-5-ol (compound 9)

(1): Synthesis of N$^1$-((2-chlorothiazol-5-yl)methyl) ethane-1,2-diamine

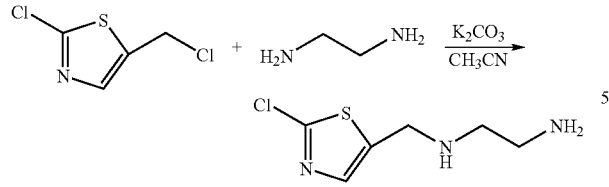

To a stirred solution of 0.03 mol of potassium carbonate and 10 ml (0.15 mol) of ethylenediamine in a 50 ml of flask placed in an ice bath, 0.03 mol of 2-chloro-5-(chloromethyl) thiazole dissolved in 15 ml of acetonitrile was added dropwise and slowly. After addition, the ice bath was removed and then the mixture was stirred for 8 hours at room temperature. After the reaction was stopped, a large amount of water was added to dissolve potassium carbonate and ethylenediamine, and the mixture was extracted with dichlormethane. The lower organic phase was collected, dried, and evaporated to dryness. The obtained product was yellow oily liquid in 70% yield.

GC MS (m/s) 191 (21) M$^+$, 132(100).

(2): Synthesis of 1-((2-chlorothiazol-5-yl)methyl)-2-(nitromethylene)-1-imidazolidine

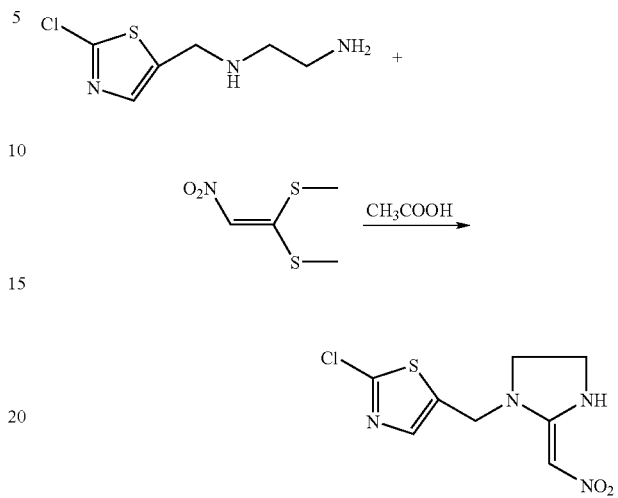

2.5 g (0.0178 mol) of 1,1-dimethylthio-2-nitroethene, 3.3 g (0.0178 mol) of N$^1$-((2-chlorothiazol-5-yl)methyl)ethane-1,2-diamine were added to 15 ml of ethanol. The resulting mixture was heated under reflux for 4 hours at 80-90° C. The mixture was then cooled to educe solid, concentrated, filtrated and dried to give a light yellow powder in 56% yield.

GC MS(m/s) 226 (24), 132(100), 77(9).

(3): Synthesis 1-((2-chlorothiazol-5-yl)methyl)-8-nitro-1,2,3,5,6,7-hexahydroimidazo[1,2-a]pyridin-5-ol

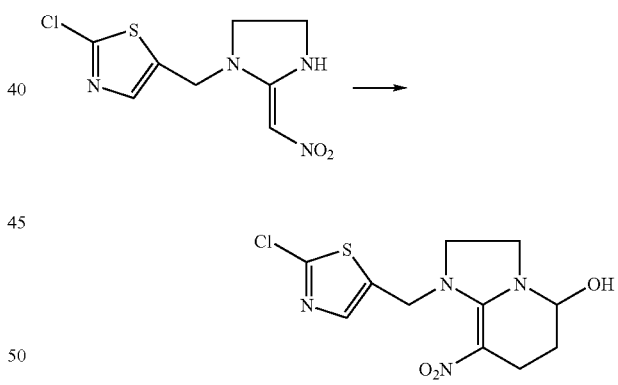

A mixture of 0.002 mol of 1-((2-chlorothiazol-5-yl)methyl)-2-(nitromethylene) imidazolidine, 15 ml of anhydrous acetonitrile, 0.15 ml of acrylaldehyde and a catalytic amount of HCl place in a 50 ml of flask was heated to 40° C. and the mixture was kept at 40° C. and stirred for 12 hours. The precipitated solid was filtrated to give a crude product. After recrystallization, the pure product was a yellow powder in 40% yield.

Mp=172-174.6° C. IR (KBr, cm$^{-1}$) 3194, 1564, 1545, 1373, 1310, 1150 Elementary analysis Calculated: C, 47.71; H, 4.14; N, 17.69; found C, 47.89; H, 4.35; N, 17.45.

EXAMPLE 10

Synthesis of 1-((2-chlorothiazolyl-5-yl)methyl)-5-ethoxy-8-nitro-1,2,3,5,6,7-hexahydroimidazo[1,2-a]pyridine (compound 10)

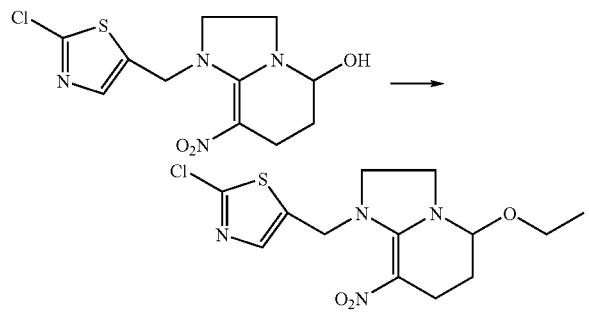

0.001 mol of compound 9 was added to a 50 ml of round-bottomed flask, and then 15 ml of methanol and a catalytic amount of glacial acetic acid were added. The resulting mixture was refluxed and followed by TLC. After the reaction was stopped, the solvent was removed. The residue was then separated to give a pure yellow powder by column chromatography in 85% yield.

Mp=128.4-129.2° C. IR (KBr) 3052 m, 2872 m, 1573 vs, 1503 s, 1312 vs, 1150 vs, 1030 s cm$^{-1}$, Elementary analysis Calculated: C, 45.28; H 4.97; N, 16.25; found C, 45.19; H, 4.92; N, 16.56.

EXAMPLE 11

Synthesis of 8-nitro-1-((tetrahydrofuran-3-yl)methyl)-1,2,3,5,6,7-hexahydro imidazo[1,2-a]pyridin-5-ol (compound 11)

(1): Synthesis of N$^1$-((tetrahydrofuran-3-yl)methyl) ethane-1,2-diamine

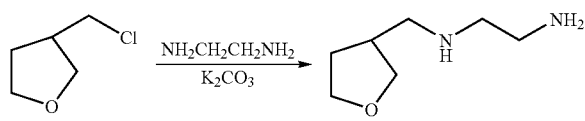

A mixture of 0.2 mol of 3-(chloromethyl)tetrahydrofuran, 200 ml of ethanol, 0.2 mol of potassium carbonate and 0.2 mol of ethylenediamine placed in a 500 ml of round-bottomed flask was refluxed for 24 hours, and then the solvent was removed. The obtained product was yellow oily liquid in 77% yield.

GC MS (m/s) 144 (67), 99(100)

(2): Synthesis of 2-(nitromethylene)-1-((tetrahydrofuran-3-yl)methyl) imidazolidine

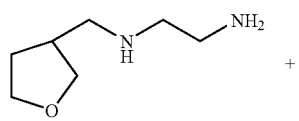

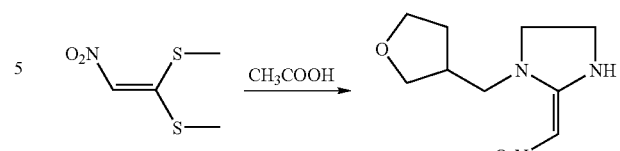

2.5 g (0.0178 mol) of 1,1-dimethylthio-2-nitroethene, 2.56 g (0.0178 mol) of N$^1$-((tetrahydrofuran-3-yl)methyl)ethane-1,2-diamine were added to 50 ml of ethanol. The resulting mixture was heated under reflux for 8 hours at 80-90 ° C. The mixture was then cooled to educe solid, concentrated, filtrated and dried to give a light yellow powder in 81% yield.

GC MS (m/s) 177(29), 99(100), 56(9).

(3): Synthesis of 8-nitro-1-((tetrahydrofuran-3-yl)methyl)-1,2,3,5,6,7-hexahydro imidazo[1,2-a]pyridin-5-ol

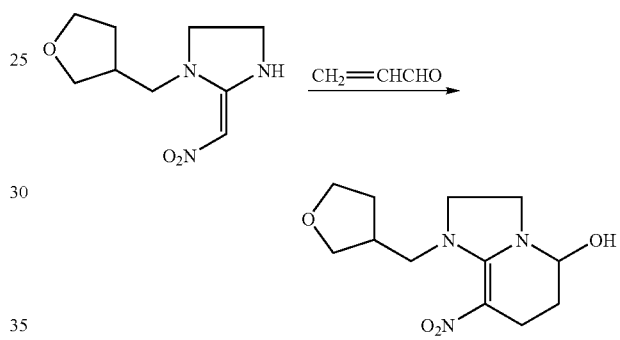

A mixture of 0.002 mol of 2-(nitromethylene)-1-((tetrahydrofuran-3-yl)methyl)imidazolidine, 15 ml of anhydrous acetonitrile, 0.15 ml of acrylaldehyde and a catalytic amount of HCl place in a 50 ml of flask was heated to 40° C. and the mixture was kept at 40° C. and stirred for 12 hours. The reaction was stopped and the solvent was removed to obtain a crude solid. After recrystallization, the pure product, which was a light yellow powder, was obtained in 67% yield.

Mp=144.2-146.1 ° C. IR (KBr, cm$^{-1}$) 3194, 1564, 1545, 1373, 1300, 1310, 1293, 1150. Elementary analysis Calculated: C, 53.52; H, 7.11; N, 15.60; found C, 53.78; H, 7.12; N, 15.35.

EXAMPLE 12

Synthesis of 8-nitro-5-propoxy-1-((tetrahydrofuran-3-yl)methyl)-1,2,3,5,6,7-hexahydroimidazo[1,2-a]pyridine (compound 12)

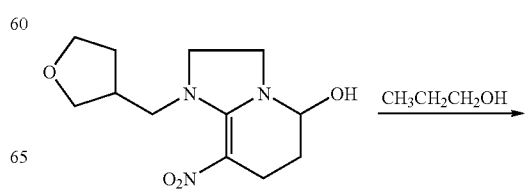

-continued

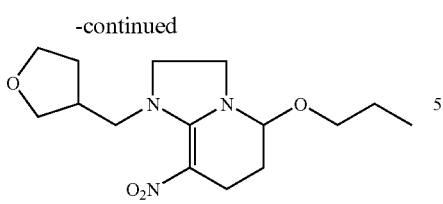

0.001 mol of compound 11 was added to a 50 ml of round-bottomed flask, and 15 ml of propanol and a catalytic amount of glacial acetic acid were added. The resulting mixture was refluxed and followed by TLC. After the reaction was stopped, the solvent was removed. The residue was then separated to give a pure yellow powder by column chromatography in 85% yield.

Mp=96.4-97.2° C. IR (KBr) 3052 m, 2872 m, 1573 vs, 1503 s, 1312 vs, 1300 m, 1297 vs, 1150 vs, 1030 s cm$^{-1}$. Elementary analysis Calculated: C, 57.86; H, 8.09; N, 13.49; found C, 58.04; H, 7.97; N, 13.42.

EXAMPLE 13

Synthesis of 1-((6-chloropyridin-3-yl)methyl)-8-nitro-1,2,3,5,6,7-hexahydro imidazo[1,2-a]pyridin-5-yl acetate (compound 13)

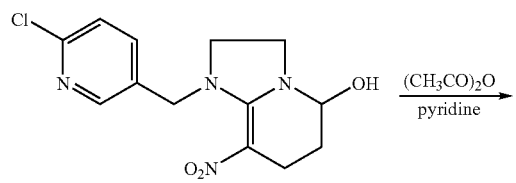

0.001 mol of compound 1 was added to a 50 ml of round-bottomed flask, and, 0.001 mol of acetic anhydride and 0.001 mol of pyridine were added. The resulting mixture was stirred at room temperature and followed by TLC. After the reaction was stopped, the solvent was removed. Then the residue was separated to give a pure light yellow powder by column chromatography in 70% yield.

Mp=134-134.7° C. IR (KBr cm$^{-1}$) 2903, 2370, 1713, 1332, 1203, 1123, 1071, 1000, 973, 830, 592 $^1$HNMR (CDCl$_3$) δ (ppm) 500 MHz: 8.33(d, J=2 Hz, 1H, Py-H), 7.88(dd, J$_1$=2 Hz, J$_2$ =8 Hz, 1H, Py-H), 7.36(d, J=8 Hz, 1H, Py-H), 4.79(d, J$_1$=15 Hz, J$_2$=15 Hz, 2H, —CH$_2$—N—), 4.48(t, J$_1$=3 Hz, J$_2$=3 Hz, 1H, —CHO—), 4.12(m, 3H, —OCOCH$_3$), 3.62(m, 4H, imidazolidine-H), 2.97(m, 2H, —CH$_2$CH$_2$—), 2.12(m, 2H, —CH$_2$CH$_2$—). Elementary analysis Calculated: C, 51.07; H 4.86; N, 15.88; found C, 51.23 ; H, 4.88, N, 15.92.

EXAMPLE 14

Synthesis of 1-((6-chloropyridin-3-yl)methyl)-5-(ethylthio)-8-nitro-1,2,3,5,6,7-hexahydroimidazo[1,2-a]pyridine (compound 14)

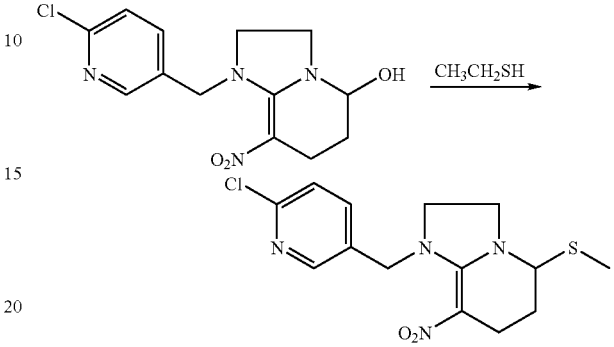

0.31 g (0.001 mol) of compound 1 was added to a 50 ml of round-bottomed flask, and 15 ml of ethanethiol and a catalytic amount of Boron trifluoride dissolved in tetrahydrofuran were added. The resulting mixture was refluxed and followed by TLC. After the reaction was stopped, the solvents were removed. The residue was then separated to give a pure yellow powder by column chromatography in 90% yield.

Mp=167.2-168.3° C.; IR (KBr, cm$^{-1}$) 2902, 1563, 1350, 1078, 900, 760, 590 $^1$HNMR (CDCl$_3$) δ (ppm) 500 MHz: 8.31(d, J=2 Hz, 1H, Py-H), 7.89(dd, J$_1$=2 Hz, J$_2$ =8 Hz, 1H, Py-H), 7.35(d, J=8 Hz, 1H, Py-H), 4.71(d, J$_1$=15 Hz, J$_2$=15 Hz, 2H, —CH$_2$—N—), 4.32(t, J$_1$=3 Hz, J$_2$=3 Hz, 1H, —CHO—), 3.60(m, 4H, imidazolidine-H), 2.89(m, 3H, —SCH$_3$), 2.90(m, 2H, —CH$_2$CH$_2$—), 1.91(m, 2H, —CH$_2$CH$_2$—) Elementary analysis Calculated: C, 49.34; H, 5.03; N 16.44; found C, 48.98; H 5.23; N, 16.48.

EXAMPLE 15

Synthesis of (E)-1-((6-chloropyridin-3-yl)methyl)-8-nitro-2,3,6,7-tetrahydro imidazo[1,2-a]pyridin-5 (1H)-one oxime (1): Synthesis of 1-((6-chloropyridin-3-yl)methyl)-8-nitro-2,3,6,7-tetrahydro imidazo[1,2-a]pyridin-5(1H)-one

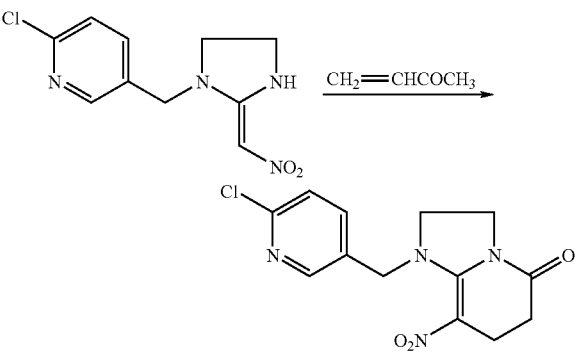

A mixture of 0.509 g (0.002 mol) of 2-chloro-5-((2-(nitromethylene)imidazolidin-1-yl) methyl)pyridine, 15 ml of anhydrous methanol and 0.002 mol methyl acrylate placed in a 50 ml of flask was refluxed for 30 hours and then separated to give a product by column chromatography in 40% yield.

Mp=167.0-168.1° C. IR (KBr, cm$^{-1}$) 3190, 1685, 1612 MS: m/z=308.

(2): Synthesis of (E)-1-((6-chloropyridin-3-yl)methyl)-8-nitro-2,3,6,7-tetrahydro imidazo[1,2-a]pyridin-5(1H)-one oxime

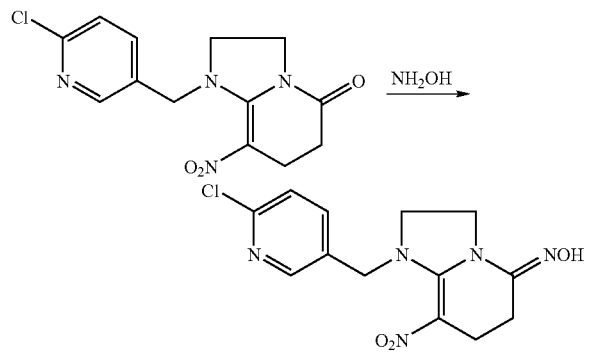

A mixture of 0.618 g (0.002 mol) of 1-((6-chloropyridin-3-yl)methyl)-8-nitro-2,3,6,7-tetrahydroimidazo[1,2-a]pyridin-5(1H)-one, 0.01 mol of hydroxylamine hydrochloride, 0.01 mol of potassium hydroxide and 20 ml of ethanol placed in a 100 ml of flask was refluxed for 24 hours. The solvent was removed and the residue was separated to give a product by column chromatography in 65% yield.

Mp=189.1-190.3° C. $^1$HNMR (CDCl$_3$) δ (ppm) 500 MHz: 8.34(d, J=2 Hz, 1H, Py-H), 7.89(dd, J$_1$=2 Hz, J$_2$=8 Hz, 1H, Py-H), 7.41(d, J=8 Hz, 1H, Py-H), 4.79(d, J$_1$=15 Hz, J$_2$=15 Hz, 2H, —CH$_2$—N—), 3.62(m, 4H, imidazolidine-H), 3.97 (m, 2H, —CH$_2$CH$_2$—), 2.96(m, 2H, —CH$_2$CH$_2$—) Elementary analysis Calculated: C, 48.23; H, 4.36; N, 21.63; found C, 48.02; H, 4.42; N, 21.92.

EXAMPLE 16

Synthesis of (E)-1-((6-chloropyridin-3-yl)methyl)-8-nitro-2,3,6,7-tetrahydro imidazo [1,2-a]pyridin-5 (1H)-one 0-methyl oxime (compound 16)

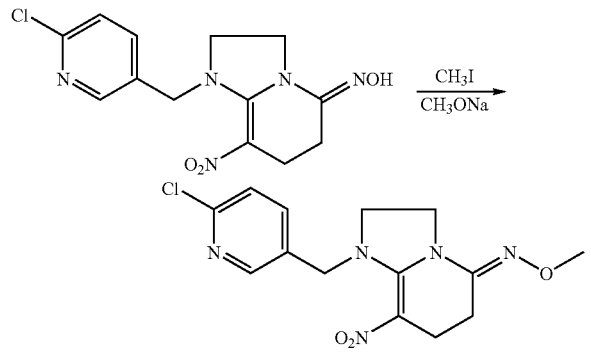

The mixture of 0.002 mol of compound 15, 0.002 mol of sodium methoxide, 0.002 mol of methyl iodide and 20 ml of methanol placed in a 100 ml of flask was stirred at room temperature for 20 hours, evaporated to remove solvent and then separated to give a pure product by column chromatography in 56% yield. Mp=156.2-156.7° C.

$^1$HNMR (CDCl$_3$) δ (ppm)500 MHz: 8.35(d, J=2 Hz, 1H, Py-H), 7.90(dd, J$_1$=2 Hz, J$_2$=8 Hz, 1H, Py-H), 7.39(d, J=8 Hz, 1H, Py-H), 4.78(d, J$_1$=15 Hz, J$_2$=15 Hz, 2H, —CH$_2$—N—), 3.62(m, 4H, imidazolidine-H), 3.99(m, 2H, —CH$_2$CH$_2$—), 3.69(s, 1H, —OCH$_3$), 2.93(m, 2H, —CH$_2$CH$_2$—). Elementary analysis Calculated: C, 49.78; H, 4.77; N, 20.73; found C, 40.89; H, 4.69; N, 21.21

EXAMPLE 17-227

According to a similar method described in example 1-16, the compound Nos. 17-227 in table 1 were obtained using proper starting materials.

The compound of the present invention can be used to control and kill general insects, including sucking insects, biting insects and other plant parasite, storage cereal insects and health hazard insects.

The examples of insects are listed as follow:

Coleoptera: *Sitophilus zeamais, Tribolium castaneum, Henosepilachna vigintioctomaculata, Agriotes fuscicollis, Monolepta hieroglyphica, Diabrotica* SPP., *Anomala cupripes, Monochamus alternatus, Echinocnemus squameus, Lyrtus hrunneus*

Lepidoptera: *Lymantria dispar, Malacosoma neustria testacea, Prodenia litura, Mamestra brassicae, Chilo stuppressalis, Ostrinia nubilalis, Cadra cautella, Adoxophyes orana, Laspeyresia splendana, Agrotis fucosa, Galleria mellonella, Plutella xylostella, Phyllocnistis citrella*

Hemiptera: *Nephotettix cincticeps, Nilaparvata lugens, Pseudococcus comstocki, Unaspis yanonensis, Myzus persicae, Aphis pomi, Lipaphis erysimi pseudobrassicae, Stephanitis nashi, Nazara* SPP., *Cimicidae, Trialeurodes vaporariorum*, and *Psylle* SPP.

Orthoptera: *Blattella germanica, Periplaneta americana, Gryllotalpa africana, Locusta migratoria.*

Isoptera: *Deucotermes speratits, Coptotermes formosanus*

Diptera: *Musca domestica, Aedes aegypti, Hylemya platura, Delia platura, Anopheles sinensi.*

The compounds in this invention have special effects to insects having a piercing-sucking or scratching mouthparts, such as aphid, leafhopper, planthopper, thrips, white fly.

These active compounds can be prepared into the customary formulations, such as solutions, emulsions, suspensions, powders, foams, pastes, granules, aerosols, natural and synthetic materials impregnated with active compounds, and micro-capsules in polymers used in the coating complex for seed, preparations used with a combustion device (such as smoking cylindrantherae, smoking can and smoking plate) and ULV cold mist and warm mist preparations. These formulations may be produced in a known manner, for example, by mixing the active compounds with extenders, which are liquid or liquefied gaseous or solid diluents or carriers, optionally with the use of surface-active agents, that is to say emulsifying agents and/or dispersing agents, and/or foam-forming agents. In the case of using water as an extender, organic solvents can, for example, also be used as auxiliary solvents It is generally proper to use liquid solvents as a diluent or carrier, for example, aromatic hydrocarbons, such as xylene, toluene and alkyl naphthalenes, chlorinated aromatic or chlorinated aliphatic hydrocarbons, such as chlorobenzenes, chloroethylenes and methylene chloride, aliphatic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, or uncommon polar solvents, such as dimethylformamide and dimethylsulfoxide, as well as water.

By liquefied gaseous diluents or carriers are meant liquids which are gaseous at normal temperature and under normal pressure, for example, aerosol propellants, such as halogenated hydrocarbons as well as butane, propane, nitrogen and carbon dioxide.

The solid carrier can use ground natural minerals, such as kaolins, clays, talcs, quartzs, attapulgites, montmorillonites or kieselguhrs; ground synthetic minerals, such as high-dispersed silicic acid, alumina and silicate. The solid carrier used for particles is crushed and fractionated natural rocks such as calcite, marble, pumice, sepiolite and dolomite, as well as synthetic granules of inorganic and organic coarse powder, and granules of organic material such as sawdust, coconut shells, maize cobs and tobacco stalks and the like.

Nonionic and anionic emulsifiers may be used as emulsifying and/or foam-forming agents, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methylcellulose.

Adhesives such as carboxymethyl cellulose and natural and synthetic polymers, (such as gum arabic, polyvinyl alcohol and polyvinyl acetate) in the form of powders, granules or emulsions can be used in the formulations It is possible to use colorants such as inorganic dyestuffs, for example, iron oxide, cobalt oxide and Prussian Blue, and organic dyestuffs, such as diazo dyestuffs or metal phthalocyanine dyestuffs, and trace nutritional agent, such as the salts of iron, manganese, boron, copper, cobalt, aluminum and zinc.

The formulations, in general, contain from 0.01 to 99.99 percent by weight of active compound, preferably 0.1-99. wt %, more preferably 0.5-90. wt %.

The active compound of the present invention can be present as a mixture with other active compounds in a commercial formulation or a use form prepared from the commercial formulation. The other compound can be insecticide, bactericide, acaricide, nematocide, fungicide, growth controller and the like. The insecticide includes phosphates, carbamate, pyrethroids, chlorinated hydrocarbons, benzoylurea, nereistoxin and material produced by microbion such as avermectin.

Furthermore, the active compound of the present invention can be present as a mixture with a synergist in a commercial formulation or a use form prepared from the commercial formulation. Synergist is used to enhance the action of active compound, so if the compound itself is active there is no need to use it.

The concentration of the active compound in the use form prepared from the commercial formulation can vary within a wide range. The active compound concentration of the formulation for use is, for example, from 0.0000001 to 100 percent by weight of active compound, preferably from 0.0001 to 1 percent by weight.

These compounds can be prepared into proper dosage forms and used by common methods Activity Test Test on the insecticidal activity of Compound Nos. 1-227

Aphis, which belongs to Homoptera and has a piercing-sucking mouthpart, is a common insect for agricultural plant. Aphis craccivoral was tested by the way of immersing.

Test method: exactly weighed various samples were independently added to N,N-dimethylformamide to form a 10 g/L stock solution. The mixture was diluted with 0.2 mL/L aqueous Triton X-100 solution to a concentration of 500 ug/mL. After stably sucking on bean sprout, the adult aphis without wings together with bean sprout was dipped into 500 ug/mL dilution, taken out after 5 seconds, and the excess dilution was sucked out with bibulous paper and the adult aphis without wings was incubated in clean vessel at a constant temperature of 23° C. Each concentration was repeated for 3 times and the control group contained 0.2 mL/L aqueous Triton X-100 solution. The number of killed aphis was counted after 24 hours to calculate the mortality. The result was shown in Table 1 bellow Planthopper, which belongs to Homoptera and has a piercing-sucking mouthpart, is a common insect for agricultural plant. *Nilaparvata lugens* was tested by the way of spraying.

Test method: the test compound was exactly formulated into a solution having a certain concentration and clean water was used as a blank control. Each process was repeated for 3 tumblers (3 times). 2 ml of solution was sprayed uniformly to each tumbler by a mini manual sprayer. 10 *Nilaparvata lugens* were introduced to every sink 6 hours before spraying. Three series of experiments were conducted. The number of killed *Nilaparvata lugens* was counted after 24 hours to calculate the mortality. The result was shown in Table 1 bellow.

TABLE 1

| Compound number | R₁ | R₂ | R₃ | R₄ | A | n | Melting point (° C.) | mortality (%) (500 ppm) Aphis | Nilaparvata-lugens |
|---|---|---|---|---|---|---|---|---|---|
| 1 | 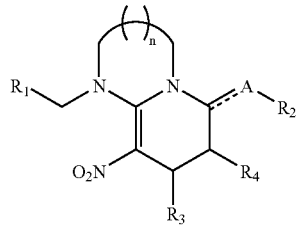 | H | H | H | —O | 0 | 169-172 | 96 | 100 |

TABLE 1-continued

[Structure: A bicyclic compound with R₁-CH₂-N, N=A-R₂, O₂N, R₃, R₄ substituents and (CH₂)ₙ bridge]

| Compound number | R₁ | R₂ | R₃ | R₄ | A | n | Melting point (° C.) | mortality (%) (500 ppm) Aphis | mortality (%) (500 ppm) *Nilaparvata-lugens* |
|---|---|---|---|---|---|---|---|---|---|
| 2 | 6-Cl-pyridin-3-yl | CH₃ | H | H | =O | 0 | 154-155 | 100 | 100 |
| 3 | 6-Cl-pyridin-3-yl | CH₂CH₃ | H | H | =O | 0 | 126-128 | 100 | 100 |
| 4 | 6-Cl-pyridin-3-yl | CH₂CH₂Cl | H | H | =O | 0 | 158-159 | 76 | 100 |
| 5 | 6-Cl-pyridin-3-yl | CH₂CF₃ | H | H | =O | 0 | 112-113 | 100 | 100 |
| 6 | 6-Cl-pyridin-3-yl | CH₂CH₂CH₃ | H | H | =O | 0 | 115-117 | 100 | 100 |
| 7 | 6-Cl-pyridin-3-yl | CH(CH₃)₂ | H | H | =O | 0 | 130-134 | 100 | 100 |
| 8 | 6-Cl-pyridin-3-yl | CH₂(CF₃)₂ | H | H | =O | 0 | 98-99 | 80 | 100 |
| 9 | 6-Cl-pyridin-3-yl | CH₂(CH₂)₂CH₃ | H | H | =O | 0 | 104-106 | 76 | 97 |
| 10 | 6-Cl-pyridin-3-yl | CH₂CH(CH₃)₂ | H | H | =O | 0 | 115-116 | 100 | 100 |
| 11 | 6-Cl-pyridin-3-yl | CH(CH₃)CH₂CH₃ | H | H | =O | 0 | 116-117 | 36 | 86 |
| 12 | 6-Cl-pyridin-3-yl | C(CH₃)₃ | H | H | =O | 0 | 145-147 | 100 | 100 |

TABLE 1-continued
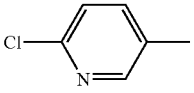
| Compound number | R₁ | R₂ | R₃ | R₄ | A | n | Melting point (° C.) | mortality (%) (500 ppm) Aphis | Nilaparvatalugens |
|---|---|---|---|---|---|---|---|---|---|
| 13 | 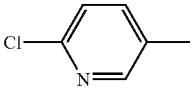 | C(CH₃)₂CCl₃ | H | H | —O | 0 | 192-193 | 56 | 90 |
| 14 | 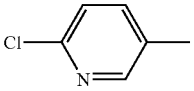 | CH₂(CH₂)₃CH₃ | H | H | —O | 0 | 83-85 | 52 | 100 |
| 15 | 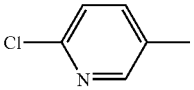 | CH₂CH₂CH(CH₃)₂ | H | H | —O | 0 | 110-111 | 67 | 97 |
| 16 | 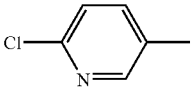 | CH(CH₃)(CH₂)₂CH₃ | H | H | —O | 0 | 125-126 | 89 | 100 |
| 17 | 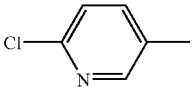 | CH₂C(CH₃)₃ | H | H | —O | 0 | 168-170 | 100 | 100 |
| 18 | 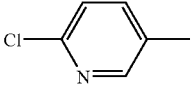 | 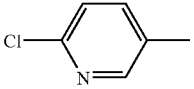 | H | H | —O | 0 | 136-137 | 23 | 67 |
| 19 | 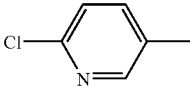 | CH₂CH=CH₂ | H | H | —O | 0 | 146-147 | 35 | 78 |
| 20 | 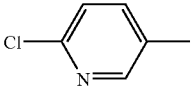 | CH₂C≡CH | H | H | —O | 0 | 168-169 | 39 | 56 |
| 21 | 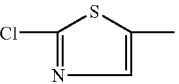 | CH₂CH₂OCH₃ | H | H | —O | 0 | 117-118 | 100 | 100 |
| 22 | | CH₂CH₂OCH₂CH₃ | H | H | —O | 0 | 108-109 | 100 | 100 |
| 23 | | H | H | H | —O | 0 | 172-174 | 87 | 100 |

TABLE 1-continued

[Structure shown with R₁-CH₂-N and N=A-R₂ in a ring, with (CH₂)ₙ bridge, O₂N substituent, R₃ and R₄ substituents]

| Compound number | R₁ | R₂ | R₃ | R₄ | A | n | Melting point (° C.) | mortality (%) (500 ppm) Aphis | Nilaparvata-lugens |
|---|---|---|---|---|---|---|---|---|---|
| 24 | 2-Cl-thiazol-5-yl | CH₃ | H | H | =O | 0 | 150-151 | 100 | 100 |
| 25 | 2-Cl-thiazol-5-yl | CH₂CH₃ | H | H | =O | 0 | 128-129 | 100 | 100 |
| 26 | 2-Cl-thiazol-5-yl | CH₂CH₂Cl | H | H | =O | 0 | 161-162 | 26 | 64 |
| 27 | 2-Cl-thiazol-5-yl | CH₂CF₃ | H | H | =O | 0 | 115-116 | 100 | 100 |
| 28 | 2-Cl-thiazol-5-yl | CH₂CH₂CH₃ | H | H | =O | 0 | 117-119 | 100 | 100 |
| 29 | 2-Cl-thiazol-5-yl | CH(CH₃)₂ | H | H | =O | 0 | 133-135 | 100 | 100 |
| 30 | 2-Cl-thiazol-5-yl | CH₂(CF₃)₂ | H | H | =O | 0 | 98-99 | 58 | 98 |
| 31 | 2-Cl-thiazol-5-yl | CH₂(CH₂)₂CH₃ | H | H | =O | 0 | 104-106 | 56 | 35 |
| 32 | 2-Cl-thiazol-5-yl | CH₂CH(CH₃)₂ | H | H | =O | 0 | 115-116 | 37 | 23 |
| 33 | 2-Cl-thiazol-5-yl | CH(CH₃)CH₂CH₃ | H | H | =O | 0 | 116-117 | 24 | 56 |
| 34 | 2-Cl-thiazol-5-yl | C(CH₃)₃ | H | H | =O | 0 | 145-147 | 100 | 100 |
| 35 | 2-Cl-thiazol-5-yl | C(CH₃)₂CCl₃ | H | H | =O | 0 | 189-190 | 98 | 100 |

TABLE 1-continued

[Structure: pyridine ring with substituents R1-CH2-N, N=A-R2, O2N, R3, R4, and (CH2)n bridge]

|  |  |  |  |  |  |  | Melting point | mortality (%) (500 ppm) | |
|---|---|---|---|---|---|---|---|---|---|
| Compound number | R1 | R2 | R3 | R4 | A | n | (°C.) | Aphis | Nilaparvata-lugens |
| 36 | 2-Cl-thiazol-5-yl | CH2(CH2)3CH3 | H | H | —O | 0 | 87-89 | 34 | 57 |
| 37 | 2-Cl-thiazol-5-yl | CH2CH2CH(CH3)2 | H | H | —O | 0 | 111-112 | 56 | 64 |
| 38 | 2-Cl-thiazol-5-yl | CH(CH3)(CH2)2CH3 | H | H | —O | 0 | 127-129 | 35 | 67 |
| 39 | 2-Cl-thiazol-5-yl | CH2C(CH3)3 | H | H | —O | 0 | 169-170 | 24 | 35 |
| 40 | 2-Cl-thiazol-5-yl | cyclohexyl | H | H | —O | 0 | 141-142 | 45 | 67 |
| 41 | 2-Cl-thiazol-5-yl | CH2CH=CH2 | H | H | —O | 0 | 152-154 | 89 | 100 |
| 42 | 2-Cl-thiazol-5-yl | CH2C≡CH | H | H | —O | 0 | 171-172 | 45 | 100 |
| 43 | 2-Cl-thiazol-5-yl | CH2CH2OCH3 | H | H | —O | 0 | 117-119 | 100 | 100 |
| 44 | 2-Cl-thiazol-5-yl | CH2CH2OCH2CH3 | H | H | —O | 0 | 112-114 | 67 | 100 |
| 45 | tetrahydrofuran-3-yl | H | H | H | —O | 0 | 144-146 | 56 | 89 |
| 46 | tetrahydrofuran-3-yl | CH3 | H | H | —O | 0 | 130-131 | 100 | 100 |
| 47 | tetrahydrofuran-3-yl | CH2CH3 | H | H | —O | 0 | 101-102 | 45 | 100 |

TABLE 1-continued
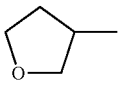
| Compound number | R₁ | R₂ | R₃ | R₄ | A | n | Melting point (° C.) | mortality (%) (500 ppm) Aphis | Nilapar- vata- lugens |
|---|---|---|---|---|---|---|---|---|---|
| 48 | 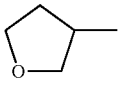 | CH₂CH₂Cl | H | H | —O | 0 | 127-129 | 3 | 0 |
| 49 | 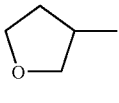 | CH₂CF₃ | H | H | —O | 0 | 97-98 | 45 | 32 |
| 50 | 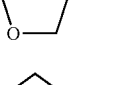 | CH₂CH₂CH₃ | H | H | —O | 0 | 96-97 | 100 | 100 |
| 51 | 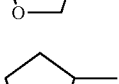 | CH(CH₃)₂ | H | H | —O | 0 | 108-109 | 34 | 23 |
| 52 | 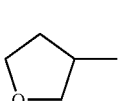 | CH₂(CF₃)₂ | H | H | —O | 0 | 82-83 | 34 | 12 |
| 53 | 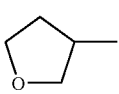 | CH₂(CH₂)₂CH₃ | H | H | —O | 0 | 96-98 | 9 | 12 |
| 54 | 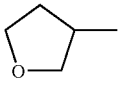 | CH₂CH(CH₃)₂ | H | H | —O | 0 | 101-102 | 23 | 34 |
| 55 | 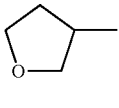 | CH(CH₃)CH₂CH₃ | H | H | —O | 0 | 111-112 | 45 | 12 |
| 56 | 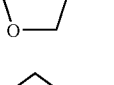 | C(CH₃)₃ | H | H | —O | 0 | 123-125 | 100 | 100 |
| 57 | 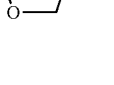 | C(CH₃)₂CCl₃ | H | H | —O | 0 | 181-184 | 34 | 38 |
| 58 |  | CH₂(CH₂)₃CH₃ | H | H | —O | 0 | 68-70 | 34 | 23 |
| 59 |  | CH(CH₃)CH₂CH₃ | H | H | —O | 0 | 98-99 | 2 | 3 |

TABLE 1-continued

|  |  |  |  |  |  |  |  | mortality (%) (500 ppm) | |
|---|---|---|---|---|---|---|---|---|---|
| Compound number | R₁ | R₂ | R₃ | R₄ | A | n | Melting point (° C.) | Aphis | *Nilaparvata-lugens* |
| 60 | 3-tetrahydrofuranyl | CH₂CH₂CH(CH₃)₂ | H | H | —O | 0 | 113-115 | 3 | 5 |
| 61 | 3-tetrahydrofuranyl | CH(CH₃)(CH₂)₂CH₃ | H | H | —O | 0 | 121-122 | 56 | 89 |
| 62 | 3-tetrahydrofuranyl | CH₂C(CH₃)₃ | H | H | —O | 0 | 136-137 | 12 | 23 |
| 63 | 3-tetrahydrofuranyl | cyclohexyl | H | H | —O | 0 | 121-125 | 2 | 6 |
| 64 | 3-tetrahydrofuranyl | CH₂CH=CH₂ | H | H | —O | 0 | 135-137 | 37 | 46 |
| 65 | 3-tetrahydrofuranyl | CH₂C≡CH | H | H | —O | 0 | 156-157 | 47 | 34 |
| 66 | 3-tetrahydrofuranyl | CH₂CH₂OCH₃ | H | H | —O | 0 | 117-118 | 100 | 100 |
| 67 | 3-tetrahydrofuranyl | CH₂CH₂OCH₂CH₃ | H | H | —O | 0 | 98-99 | 100 | 100 |
| 68 | 3-tetrahydrofuranyl | H | Me | H | —O | 0 | 146-147 | 2 | 7 |
| 69 | 6-chloro-3-pyridyl | H | Me | H | —O | 0 | 164-165 | 45 | 56 |
| 70 | 2-chloro-5-thiazolyl | H | Me | H | —O | 0 | 165-166 | 33 | 12 |
| 71 | 6-chloro-3-pyridyl | H | H | H | —O | 1 | 172-173 | 6 | 0 |

TABLE 1-continued

|  |  |  |  |  |  |  |  | mortality (%) (500 ppm) | |
|---|---|---|---|---|---|---|---|---|---|
| Compound number | $R_1$ | $R_2$ | $R_3$ | $R_4$ | A | n | Melting point (° C.) | Aphis | *Nilaparvatalugens* |
| 72 | 6-Cl-pyridin-3-yl | $CH_3$ | H | H | =O | 1 | 156-157 | 35 | 100 |
| 73 | 6-Cl-pyridin-3-yl | $CH_2CH_3$ | H | H | =O | 1 | 129-130 | 34 | 56 |
| 74 | 6-Cl-pyridin-3-yl | $CH_2CH_2Cl$ | H | H | =O | 1 | 160-161 | 12 | 13 |
| 75 | 6-Cl-pyridin-3-yl | $CH_2CF_3$ | H | H | =O | 1 | 114-115 | 88 | 100 |
| 76 | 6-Cl-pyridin-3-yl | $CH_2CH_2CH_3$ | H | H | =O | 1 | 118-119 | 100 | 100 |
| 77 | 6-Cl-pyridin-3-yl | $CH(CH_3)_2$ | H | H | =O | 1 | 135-137 | 56 | 78 |
| 78 | 6-Cl-pyridin-3-yl | $CH_2(CF_3)_2$ | H | H | =O | 1 | 102-103 | 68 | 51 |
| 79 | 6-Cl-pyridin-3-yl | $CH_2(CH_2)_2CH_3$ | H | H | =O | 1 | 114-115 | 52 | 61 |
| 80 | 6-Cl-pyridin-3-yl | $CH_2CH(CH_3)_2$ | H | H | =O | 1 | 124-126 | 23 | 34 |
| 81 | 6-Cl-pyridin-3-yl | $CH(CH_3)CH_2CH_3$ | H | H | =O | 1 | 127-128 | 12 | 8 |
| 82 | 6-Cl-pyridin-3-yl | $C(CH_3)_3$ | H | H | =O | 1 | 195-197 | 12 | 34 |

TABLE 1-continued

| Compound number | R₁ | R₂ | R₃ | R₄ | A | n | Melting point (°C.) | mortality (%) (500 ppm) Aphis | Nilaparvatalugens |
|---|---|---|---|---|---|---|---|---|---|
| 83 | 6-Cl-pyridin-3-yl | CH₂CH₂OCH₃ | H | H | =O | 1 | 167-168 | 38 | 26 |
| 84 | 6-Cl-pyridin-3-yl | CH₂CH₂OCH₂CH₃ | H | H | =O | 1 | 169-170 | 26 | 39 |
| 85 | 2-Cl-thiazol-5-yl | H | H | H | =O | 1 | 175-176 | 12 | 23 |
| 86 | 2-Cl-thiazol-5-yl | CH₃ | H | H | =O | 1 | 158-159 | 100 | 100 |
| 87 | 2-Cl-thiazol-5-yl | CH₂CH₃ | H | H | =O | 1 | 128-130 | 100 | 100 |
| 88 | 2-Cl-thiazol-5-yl | CH₂CH₂Cl | H | H | =O | 1 | 165-168 | 23 | 34 |
| 89 | 2-Cl-thiazol-5-yl | CH₂CF₃ | H | H | =O | 1 | 119-120 | 100 | 100 |
| 90 | 2-Cl-thiazol-5-yl | CH₂CH₂CH₃ | H | H | =O | 1 | 123-125 | 34 | 51 |
| 91 | 2-Cl-thiazol-5-yl | CH(CH₃)₂ | H | H | =O | 1 | 138-139 | 69 | 71 |
| 92 | 2-Cl-thiazol-5-yl | CH₂(CF₃)₂ | H | H | =O | 1 | 112-116 | 6 | 5 |
| 93 | 2-Cl-thiazol-5-yl | CH₂(CH₂)₂CH₃ | H | H | =O | 1 | 118-119 | 7 | 8 |
| 94 | 2-Cl-thiazol-5-yl | CH₂CH(CH₃)₂ | H | H | =O | 1 | 128-129 | 8 | 3 |

TABLE 1-continued

[Structure: pyridine derivative with R1-CH2-N, ring with n CH2 groups, N=A-R2, O2N, R3, R4 substituents]

| Compound number | R₁ | R₂ | R₃ | R₄ | A | n | Melting point (° C.) | mortality (%) (500 ppm) Aphis | mortality (%) (500 ppm) Nilaparvatalugens |
|---|---|---|---|---|---|---|---|---|---|
| 95 | 2-Cl-thiazol-5-yl | CH(CH₃)CH₂CH₃ | H | H | =O | 1 | 131-133 | 4 | 8 |
| 96 | 2-Cl-thiazol-5-yl | C(CH₃)₃ | H | H | =O | 1 | 199-200 | 80 | 100 |
| 97 | 2-Cl-thiazol-5-yl | CH₂CH₂OCH₃ | H | H | =O | 1 | 169-170 | 78 | 100 |
| 98 | 2-Cl-thiazol-5-yl | CH₂CH₂OCH₂CH₃ | H | H | =O | 1 | 165-167 | 4 | 7 |
| 99 | tetrahydrofuran-3-yl | H | H | H | =O | 1 | 162-163 | 6 | 7 |
| 100 | tetrahydrofuran-3-yl | CH₃ | H | H | =O | 1 | 143-145 | 3 | 8 |
| 101 | tetrahydrofuran-3-yl | CH₂CH₃ | H | H | =O | 1 | 113-112 | 76 | 90 |
| 102 | tetrahydrofuran-3-yl | CH₂CH₂Cl | H | H | =O | 1 | 146-148 | 0 | 89 |
| 103 | tetrahydrofuran-3-yl | CH₂CF₃ | H | H | =O | 1 | 102-103 | 6 | 100 |
| 104 | tetrahydrofuran-3-yl | CH₂CH₂CH₃ | H | H | =O | 1 | 108-109 | 3 | 24 |
| 105 | tetrahydrofuran-3-yl | CH(CH₃)₂ | H | H | =O | 1 | 117-119 | 10 | 98 |
| 106 | tetrahydrofuran-3-yl | CH₂(CF₃)₂ | H | H | =O | 1 | 98-99 | 45 | 100 |

TABLE 1-continued

| Compound number | R₁ | R₂ | R₃ | R₄ | A | n | Melting point (° C.) | mortality (%) (500 ppm) Aphis | mortality (%) (500 ppm) *Nilaparvata-lugens* |
|---|---|---|---|---|---|---|---|---|---|
| 107 | tetrahydrofuran-3-ylmethyl | CH₂(CH₂)₂CH₃ | H | H | —O | 1 | 104-106 | 7 | 0 |
| 108 | tetrahydrofuran-3-ylmethyl | CH₂CH(CH₃)₂ | H | H | —O | 1 | 109-111 | 1 | 9 |
| 109 | tetrahydrofuran-3-ylmethyl | CH(CH₃)CH₂CH₃ | H | H | —O | 1 | 113-115 | 2 | 10 |
| 110 | tetrahydrofuran-3-ylmethyl | C(CH₃)₃ | H | H | —O | 1 | 178-179 | 67 | 98 |
| 111 | 6-chloropyridin-3-yl | H₂C-C₆H₅ | H | H | —O | 0 | 187-189 | 1 | 23 |
| 112 | 6-chloropyridin-3-yl | C₆H₅ | H | H | —O | 0 | 193-195 | 38 | 75 |
| 113 | 6-chloropyridin-3-yl | COCH₃ | H | H | —O | 0 | 167-169 | 45 | 77 |
| 114 | 6-chloropyridin-3-yl | COCH₂CH₃ | H | H | —O | 0 | 165-166 | 56 | 88 |
| 115 | 6-chloropyridin-3-yl | COCCl₃ | H | H | —O | 0 | 194-196 | 0 | 33 |
| 116 | 6-chloropyridin-3-yl | COCF₃ | H | H | —O | 0 | 135-137 | 2 | 45 |
| 117 | 6-chloropyridin-3-yl | SO₂CH₃ | H | H | —O | 0 | 178-179 | 19 | 65 |

TABLE 1-continued
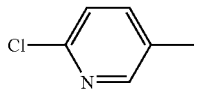
| Compound number | R₁ | R₂ | R₃ | R₄ | A | n | Melting point (° C.) | mortality (%) (500 ppm) Aphis | mortality (%) (500 ppm) *Nilaparvata-lugens* |
|---|---|---|---|---|---|---|---|---|---|
| 118 |  | SO₂CF₃ | H | H | —O | 0 | 167-168 | 81 | 100 |
| 119 | 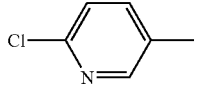 | 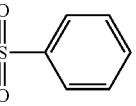 | H | H | —O | 0 | 196-197 | 3 | 23 |
| 120 | 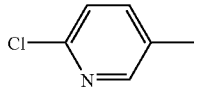 | 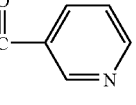 | H | H | —O | 0 | 182-184 | 1 | 5 |
| 121 | 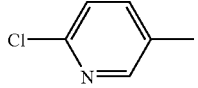 | 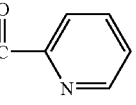 | H | H | —O | 0 | 183-185 | 0 | 8 |
| 122 | 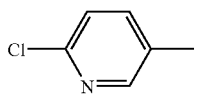 | 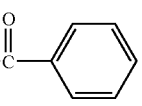 | H | H | —O | 0 | 176-178 | 56 | 23 |
| 123 | 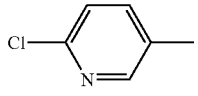 | 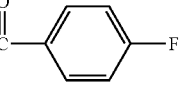 | H | H | —O | 0 | 176-177 | 56 | 100 |
| 124 | 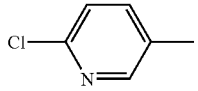 | 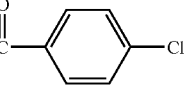 | H | H | —O | 0 | 183-186 | 22 | 0 |
| 125 | 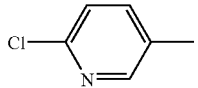 | 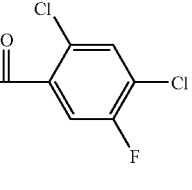 | H | H | —O | 0 | 156-158 | 67 | 92 |
| 126 | 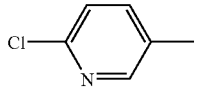 | 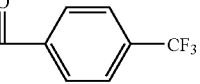 | H | H | —O | 0 | 178-179 | 93 | 100 |

TABLE 1-continued

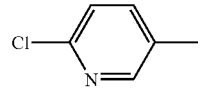

| Compound number | R₁ | R₂ | R₃ | R₄ | A | n | Melting point (° C.) | mortality (%) (500 ppm) Aphis | *Nilaparvatalugens* |
|---|---|---|---|---|---|---|---|---|---|
| 127 | 6-chloropyridin-3-yl-methyl | 2,4,5-trifluorobenzoyl | H | H | —O | 0 | 180-181 | 45 | 78 |
| 128 | 6-chloropyridin-3-yl-methyl | 2,3,4,5-tetrafluorobenzoyl | H | H | —O | 0 | 193-195 | 0 | 21 |
| 129 | 6-chloropyridin-3-yl-methyl | 2-fluorobenzoyl | H | H | —O | 0 | 196-197 | 0 | 34 |
| 130 | 6-chloropyridin-3-yl-methyl | 2,5-difluoro-3-nitrobenzoyl | H | H | —O | 0 | 201-202 | 23 | 67 |
| 131 | 6-chloropyridin-3-yl-methyl | 3,4-dichlorobenzoyl | H | H | —O | 0 | 197-199 | 3 | 0 |
| 132 | 6-chloropyridin-3-yl-methyl | CH₃ | H | H | —S | 0 | 167-168 | 100 | 100 |
| 133 | 6-chloropyridin-3-yl-methyl | CH₂CH₃ | H | H | —S | 0 | 145-147 | 100 | 100 |
| 134 | 6-chloropyridin-3-yl-methyl | CH₂CH₂Cl | H | H | —S | 0 | 178-179 | 34 | 78 |

TABLE 1-continued

[Structure: bicyclic ring system with R₁CH₂–N, N=A–R₂, O₂N substituent, R₃, R₄ substituents, and (CH₂)ₙ bridge]

| Compound number | R₁ | R₂ | R₃ | R₄ | A | n | Melting point (° C.) | mortality (%) (500 ppm) Aphis | mortality (%) (500 ppm) Nilaparvata-lugens |
|---|---|---|---|---|---|---|---|---|---|
| 135 | 6-Cl-pyridin-3-yl | CH₂CF₃ | H | H | —S | 0 | 156-158 | 98 | 100 |
| 136 | 6-Cl-pyridin-3-yl | CH₂CH₂CH₃ | H | H | —S | 0 | 136-138 | 100 | 100 |
| 137 | 6-Cl-pyridin-3-yl | CH(CH₃)₂ | H | H | —S | 0 | 151-152 | 89 | 100 |
| 138 | 6-Cl-pyridin-3-yl | CH₂(CF₃)₂ | H | H | —S | 0 | 137-138 | 45 | 98 |
| 139 | 6-Cl-pyridin-3-yl | CH₂(CH₂)₂CH₃ | H | H | —S | 0 | 124-125 | 34 | 78 |
| 140 | 6-Cl-pyridin-3-yl | CH₂CH(CH₃)₂ | H | H | —S | 0 | 135-138 | 67 | 78 |
| 141 | 6-Cl-pyridin-3-yl | CH(CH₃)CH₂CH₃ | H | H | —S | 0 | 139-140 | 56 | 89 |
| 142 | 6-Cl-pyridin-3-yl | C(CH₃)₃ | H | H | —S | 0 | 160-161 | 67 | 88 |
| 143 | 6-Cl-pyridin-3-yl | CH₂(CH₂)₃CH₃ | H | H | —S | 0 | 112-113 | 23 | 34 |
| 144 | 6-Cl-pyridin-3-yl | CH(CH₃)CH₂CH₃ | H | H | —S | 0 | 128-129 | 12 | 56 |
| 145 | 6-Cl-pyridin-3-yl | CH₂CH₂CH(CH₃)₂ | H | H | —S | 0 | 131-132 | 67 | 78 |

TABLE 1-continued

[Structure: A pyridine-like ring system with R1-CH2-N on left connected via (CH2)n to another N, which double-bonds to A-R2; ring has O2N, R3, R4 substituents]

| | | | | | | mortality (%) (500 ppm) | |
|---|---|---|---|---|---|---|---|
| Compound number | R₁ | R₂ | R₃ | R₄ | A | n | Melting point (° C.) | Aphis | Nilaparvata-lugens |

| Compound number | R₁ | R₂ | R₃ | R₄ | A | n | Melting point (° C.) | Aphis | Nilaparvata-lugens |
|---|---|---|---|---|---|---|---|---|---|
| 146 | 2-Cl-pyridin-5-yl | CH(CH₃)(CH₂)₂CH₃ | H | H | —S | 0 | 129-130 | 35 | 97 |
| 147 | 2-Cl-pyridin-5-yl | CH₂C(CH₃)₃ | H | H | —S | 0 | 138-139 | 56 | 99 |
| 148 | 2-Cl-pyridin-5-yl | CH₂CH₂OCH₃ | H | H | —S | 0 | 128-129 | 67 | 89 |
| 149 | 2-Cl-pyridin-5-yl | CH₂CH₂OCH₂CH₃ | H | H | —S | 0 | 126-127 | 98 | 100 |
| 150 | 2-Cl-thiazol-5-yl | phenyl-CH₂ | H | H | —O | 0 | 186-187 | 3 | 67 |
| 151 | 2-Cl-thiazol-5-yl | phenyl | H | H | —O | 0 | 197-199 | 2 | 16 |
| 152 | 2-Cl-thiazol-5-yl | COCH₃ | H | H | —O | 0 | 169-170 | 3 | 0 |
| 153 | 2-Cl-thiazol-5-yl | COCH₂CH₃ | H | H | —O | 0 | 168-169 | 29 | 38 |
| 154 | 2-Cl-thiazol-5-yl | COCCl₃ | H | H | —O | 0 | 197-198 | 93 | 100 |
| 155 | 2-Cl-thiazol-5-yl | COCF₃ | H | H | —O | 0 | 138-139 | 48 | 90 |
| 156 | 2-Cl-thiazol-5-yl | SO₂CH₃ | H | H | —O | 0 | 178-180 | 78 | 92 |
| 157 | 2-Cl-thiazol-5-yl | SO₂CF₃ | H | H | —O | 0 | 169-171 | 56 | 100 |

TABLE 1-continued

[Structure diagram showing core scaffold with R1, R2, R3, R4, A, n substituents, with O2N group]

| Compound number | R1 | R2 | R3 | R4 | A | n | Melting point (° C.) | mortality (%) (500 ppm) Aphis | mortality (%) (500 ppm) Nilaparvata-lugens |
|---|---|---|---|---|---|---|---|---|---|
| 158 | 2-Cl-thiazol-5-yl | -S(O)₂-phenyl | H | H | =O | 0 | 198-199 | 6 | 7 |
| 159 | 2-Cl-thiazol-5-yl | -C(O)-pyridin-3-yl | H | H | =O | 0 | 186-187 | 0 | 8 |
| 160 | 2-Cl-thiazol-5-yl | -C(O)-pyridin-2-yl | H | H | =O | 0 | 187-189 | 4 | 8 |
| 161 | 2-Cl-thiazol-5-yl | -C(O)-phenyl | H | H | =O | 0 | 177-178 | 3 | 5 |
| 162 | 2-Cl-thiazol-5-yl | -C(O)-(4-F-phenyl) | H | H | =O | 0 | 179-180 | 34 | 98 |
| 163 | 2-Cl-thiazol-5-yl | -C(O)-(4-Cl-phenyl) | H | H | =O | 0 | 187-188 | 1 | 0 |
| 164 | 2-Cl-thiazol-5-yl | -C(O)-(2,4-diCl-5-F-phenyl) | H | H | =O | 0 | 163-165 | 59 | 78 |
| 165 | 2-Cl-thiazol-5-yl | -C(O)-(4-CF₃-phenyl) | H | H | =O | 0 | 184-188 | 90 | 100 |
| 166 | 2-Cl-thiazol-5-yl | -C(O)-(2,4,5-triF-phenyl) | H | H | =O | 0 | 185-188 | 0 | 45 |

TABLE 1-continued
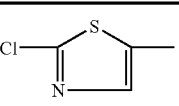
| Compound number | R₁ | R₂ | R₃ | R₄ | A | n | Melting point (° C.) | mortality (%) (500 ppm) Aphis | *Nilaparvatalugens* |
|---|---|---|---|---|---|---|---|---|---|
| 167 | 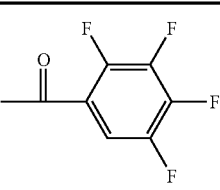 | 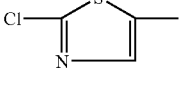 | H | H | —O | 0 | 193-194 | 12 | 4 |
| 168 | 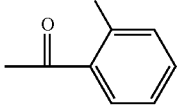 | 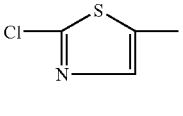 | H | H | —O | 0 | 198-199 | 56 | 100 |
| 169 | 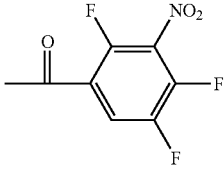 | 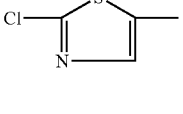 | H | H | —O | 0 | 207-209 | 2 | 13 |
| 170 | 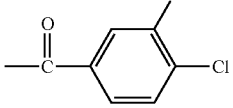 | 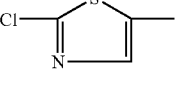 | H | H | —O | 0 | 195-196 | 2 | 0 |
| 171 | 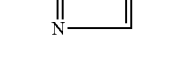 | CH₃ | H | H | —S | 0 | 169-170 | 97 | 100 |
| 172 | 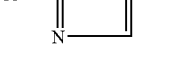 | CH₂CH₃ | H | H | —S | 0 | 148-149 | 100 | 100 |
| 173 | 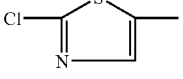 | CH₂CH₂Cl | H | H | —S | 0 | 179-181 | 45 | 56 |
| 174 | 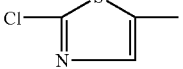 | CH₂CF₃ | H | H | —S | 0 | 159-161 | 67 | 100 |
| 175 |  | CH₂CH₂CH₃ | H | H | —S | 0 | 139-140 | 89 | 100 |

TABLE 1-continued

|  | | | | | | | mortality (%) (500 ppm) | |
|---|---|---|---|---|---|---|---|---|
| Compound number | R$_1$ | R$_2$ | R$_3$ | R$_4$ | A | n | Melting point (° C.) | Aphis | Nilaparvatalugens |
| 176 | 2-chloro-thiazol-5-yl | CH(CH$_3$)$_2$ | H | H | —S | 0 | 155-156 | 78 | 98 |
| 177 | 2-chloro-thiazol-5-yl | CH$_2$(CF$_3$)$_2$ | H | H | —S | 0 | 141-142 | 56 | 65 |
| 178 | 2-chloro-thiazol-5-yl | CH$_2$(CH$_2$)$_2$CH$_3$ | H | H | —S | 0 | 127-128 | 23 | 12 |
| 179 | 2-chloro-thiazol-5-yl | CH$_2$CH(CH$_3$)$_2$ | H | H | —S | 0 | 138-139 | 12 | 56 |
| 180 | 2-chloro-thiazol-5-yl | CH(CH$_3$)CH$_2$CH$_3$ | H | H | —S | 0 | 142-143 | 34 | 78 |
| 181 | 2-chloro-thiazol-5-yl | C(CH$_3$)$_3$ | H | H | —S | 0 | 166-167 | 45 | 78 |
| 182 | 2-chloro-thiazol-5-yl | CH$_2$(CH$_2$)$_3$CH$_3$ | H | H | —S | 0 | 117-119 | 67 | 87 |
| 183 | 2-chloro-thiazol-5-yl | CH$_2$CH$_2$CH(CH$_3$)$_2$ | H | H | —S | 0 | 136-137 | 23 | 34 |
| 184 | 2-chloro-thiazol-5-yl | CH(CH$_3$)(CH$_2$)$_2$CH$_3$ | H | H | —S | 0 | 131-132 | 12 | 35 |
| 185 | 2-chloro-thiazol-5-yl | CH$_2$C(CH$_3$)$_3$ | H | H | —S | 0 | 143-144 | 36 | 86 |
| 186 | 2-chloro-thiazol-5-yl | CH$_2$CH$_2$OCH$_3$ | H | H | —S | 0 | 132-133 | 97 | 100 |
| 187 | 2-chloro-thiazol-5-yl | CH$_2$CH$_2$OCH$_2$CH$_3$)$_3$ | H | H | —S | 0 | 127-129 | 34 | 97 |

TABLE 1-continued
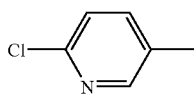
| Compound number | R₁ | R₂ | R₃ | R₄ | A | n | Melting point (° C.) | mortality (%) (500 ppm) Aphis | *Nilaparvatalugens* |
|---|---|---|---|---|---|---|---|---|---|
| 188 | 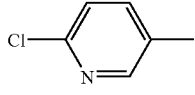 | H | H | H | =N | 0 | 189-190 | 55 | 67 |
| 189 | 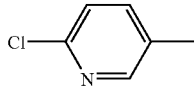 | CH₃ | H | H | =N | 0 | 156-157 | 100 | 100 |
| 190 | 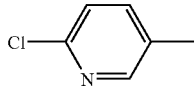 | CH₂CH₃ | H | H | =N | 0 | 146-147 | 89 | 100 |
| 191 | 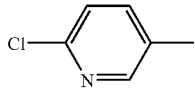 | CH₂CH₂Cl | H | H | =N | 0 | 176-177 | 53 | 78 |
| 192 | 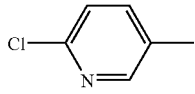 | CH₂CH₂CH₃ | H | H | =N | 0 | 125-127 | 86 | 100 |
| 193 | 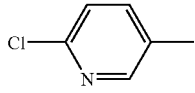 | CH(CH₃)₂ | H | H | =N | 0 | 137-137 | 93 | 98 |
| 194 | 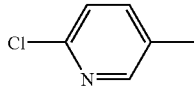 | CH₂CH₂CH₂CH₃ | H | H | =N | 0 | 118-119 | 34 | 45 |
| 195 | 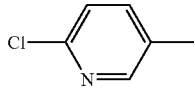 | CH₂(CH₂)₃CH₃ | H | H | =N | 0 | 101-102 | 46 | 78 |
| 196 | 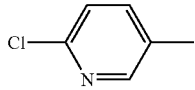 | CH₂CH₂CH(CH₃)₂ | H | H | =N | 0 | 123-124 | 12 | 25 |
| 197 | 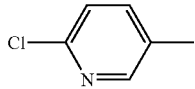 | CH(CH₃)(CH₂)₂CH₃ | H | H | =N | 0 | 131-132 | 8 | 56 |
| 198 |  | CH₂C(CH₃)₃ | H | H | =N | 0 | 143-144 | 39 | 89 |

TABLE 1-continued
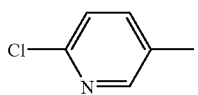
| Compound number | R₁ | R₂ | R₃ | R₄ | A | n | Melting point (° C.) | mortality (%) (500 ppm) Aphis | *Nilaparvata-lugens* |
|---|---|---|---|---|---|---|---|---|---|
| 199 | 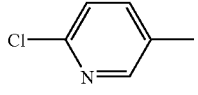 | CH₂CH₂OCH₃ | H | H | =N | 0 | 121-123 | 16 | 36 |
| 200 | 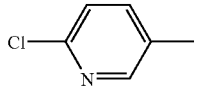 | CH₂CH₂OCH₂CH₃)₃ | H | H | =N | 0 | 119-120 | 45 | 78 |
| 201 | 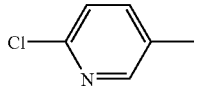 | H | H | H | =N | 1 | 193-194 | 54 | 55 |
| 202 | 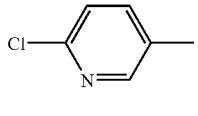 | CH₃ | H | H | =N | 1 | 163-165 | 89 | 98 |
| 203 | 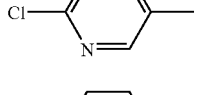 | CH₂CH₃ | H | H | =N | 1 | 151-155 | 92 | 100 |
| 204 | 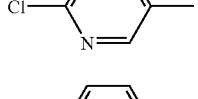 | CH₂CH₂Cl | H | H | =N | 1 | 178-179 | 46 | 78 |
| 205 | 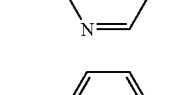 | CH₂CH₂CH₃ | H | H | =N | 1 | 128-129 | 35 | 100 |
| 206 | 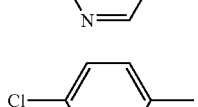 | CH(CH₃)₂ | H | H | =N | 1 | 139-140 | 56 | 98 |
| 207 | 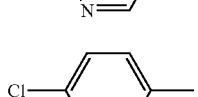 | CH₂CH₂CH₂CH₃ | H | H | =N | 1 | 120-122 | 14 | 45 |
| 208 | 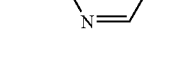 | CH₂(CH₂)₃CH₃ | H | H | =N | 1 | 104-106 | 35 | 67 |
| 209 | | CH₂CH₂CH(CH₃)₂ | H | H | =N | 1 | 126-127 | 23 | 26 |

TABLE 1-continued

[Structure: ring with R1-CH2-N, N=A-R2, with (CH2)n bridge, O2N substituent, R3, R4 substituents]

| Compound number | R1 | R2 | R3 | R4 | A | n | Melting point (°C.) | Aphis | *Nilaparvata-lugens* |
|---|---|---|---|---|---|---|---|---|---|
| | | | | | | | | \multicolumn{2}{c}{mortality (%) (500 ppm)} |
| 210 | 6-chloropyridin-3-yl | $CH(CH_3)(CH_2)_2CH_3$ | H | H | =N | 1 | 135-136 | 7 | 77 |
| 211 | 6-chloropyridin-3-yl | $CH_2C(CH_3)_3$ | H | H | =N | 1 | 147-148 | 34 | 56 |
| 212 | 2-chlorothiazol-5-yl | H | H | H | =N | 0 | 203-205 | 34 | 23 |
| 213 | 2-chlorothiazol-5-yl | $CH_3$ | H | H | =N | 0 | 169-170 | 32 | 78 |
| 214 | 2-chlorothiazol-5-yl | $CH_2CH_3$ | H | H | =N | 0 | 157-158 | 55 | 90 |
| 215 | 2-chlorothiazol-5-yl | $CH_2CH_2Cl$ | H | H | =N | 0 | 182-183 | 9 | 97 |
| 216 | 2-chlorothiazol-5-yl | $CH_2CH_2CH_2CH_3$ | H | H | =N | 0 | 136-138 | 66 | 98 |
| 217 | 2-chlorothiazol-5-yl | $CH_2CH_2CH_3$ | H | H | =N | 0 | 145-146 | 23 | 100 |
| 218 | 2-chlorothiazol-5-yl | $CH_2(CH_2)_3CH_3$ | H | H | =N | 0 | 129-130 | 45 | 67 |
| 219 | 2-chlorothiazol-5-yl | $CH(CH_3)_2$ | H | H | =N | 0 | 142-145 | 34 | 45 |
| 220 | 2-chlorothiazol-5-yl | H | H | H | =N | 1 | 205-207 | 16 | 56 |
| 221 | 2-chlorothiazol-5-yl | $CH_3$ | H | H | =N | 1 | 172-176 | 4 | 67 |

TABLE 1-continued

[Chemical structure: a bicyclic ring system with $R_1$-CH$_2$-N on left, $(CH_2)_n$ bridge at top, N=A-$R_2$ on right, $O_2N$ and $R_3$, $R_4$ substituents]

| Compound number | $R_1$ | $R_2$ | $R_3$ | $R_4$ | A | n | Melting point (°C.) | mortality (%) (500 ppm) Aphis | mortality (%) (500 ppm) Nilaparvata-lugens |
|---|---|---|---|---|---|---|---|---|---|
| 222 | Cl-thiazole | CH$_2$CH$_3$ | H | H | =N | 1 | 162-163 | 4 | 89 |
| 223 | Cl-thiazole | CH$_2$CH$_2$Cl | H | H | =N | 1 | 185-186 | 5 | 76 |
| 224 | Cl-thiazole | CH$_2$CH$_2$CH$_2$CH$_3$ | H | H | =N | 1 | 137-138 | 45 | 66 |
| 225 | Cl-thiazole | CH$_2$CH$_2$CH$_3$ | H | H | =N | 1 | 147-148 | 35 | 78 |
| 226 | Cl-thiazole | CH$_2$(CH$_2$)$_3$CH$_3$ | H | H | =N | 1 | 133-135 | 22 | 57 |
| 227 | Cl-thiazole | CH(CH$_3$)$_2$ | H | H | =N | 1 | 146-148 | 100 | 100 |

COMPOSITION EXAMPLE 1

(a) Oily Suspension

| | |
|---|---|
| Any one of compounds 1-16 | 25 wt % |
| Polyoxyethylene sorbital hexaoleate | 5 wt % |
| Higher aliphatic hydrocarbon oil | 70 wt % |

Each of the components was ground in a sand mill until the solid granules were reduced to less than about 5 micrometer. The resulting viscous suspension can be used directly or may be used after it was emulsified in water.

(b) Aqueous Suspension

| | |
|---|---|
| Any one of compounds 1-16 | 25 wt % |
| Hydrate attapulagit | 3 wt % |
| Calcium lignosulphonate | 10 wt % |
| Sodium dihydrogen phosphate | 0.5 wt % |
| Water | 61.5 wt % |

Each of the components was ground in a ball mill until the solid granules were reduced to less than about 10 micrometer. The aqueous suspension can be used directly.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

We claim:
1. A derivative of the following formula,

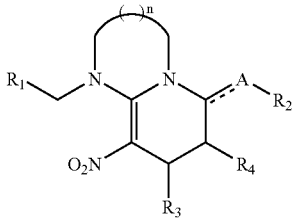

(I)

or an agriculturally acceptable salt thereof, wherein
$R_1$ represents a substituted or unsubstituted 5- or 6-membered heterocyclyl containing nitrogen, oxygen and/or sulfur, wherein the substituents are one to three substituents selected from the group consisting of a halogen atom, $C_{1-4}$ haloalkyl and $C_{1-4}$ haloalkoxyl;
$R_2$ represents a hydrogen atom, a saturated or unsaturated $C_{1-8}$ hydrocarbyl group, a saturated or unsaturated $C_{1-8}$ halogenated hydrocarbyl group, —$CH_2CH_2OCH_2CH_3$, —$CH_2CH_2OCH_3$, a substituted or unsubstituted phenyl group, a substituted or unsubstituted benzyl group, a substituted or unsubstituted $C_{1-8}$ alkoxyl group which is saturated or unsaturated, wherein the substituents are one to three substituents selected from the group consisting of halogen, $C_{1-4}$ haloalkyl and $C_{1-4}$ haloalkoxyl; or $R_2$ represents a group of the following formula:

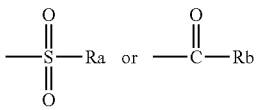

wherein Ra represents a methyl group, a trifluoromethyl group or a phenyl group; Rb represents a methyl group, a trifluoromethyl group, a pyridyl group, a phenyl group or a phenyl group substituted with a halogen atom and/or a nitro group;
$R_3$ and $R_4$ independently represents a hydrogen atom, a substituted or unsubstituted $C_{1-3}$ alkyl group, wherein the substituents are one to three substituents selected from the group consisting of a halogen atom, $C_{1-4}$ haloalkyl and $C_{1-4}$ haloalkoxyl;
A represents O, S or N; and
n represents 0 or 1.
2. The derivative according to claim 1, wherein $R_1$ represents a pyridyl group, a thiazolyl group, a pyrimidinyl group, a tetrahydrofuryl group, an oxazolyl group, or the chlorides thereof.
3. The derivative according to claim 2, wherein $R_1$ represents

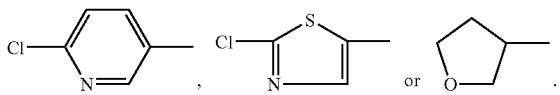

4. The derivative according to claim 1, wherein $R_2$ represents a hydrogen atom, a saturated or unsaturated $C_{1-8}$ hydrocarbyl group, a saturated or unsaturated $C_{1-8}$ halogenated hydrocarbyl group, —$CH_2CH_2OCH_2CH_3$, —$CH_2CH_2OCH_3$, or a saturated or unsaturated $C_{1-8}$ alkoxyl group.
5. The derivative according to claim 1 which has the structure of formula II

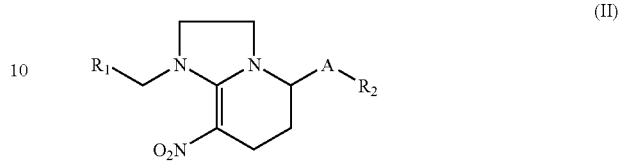

(II)

wherein $R_1$, $R_2$ and A are defined as above.
6. The derivative according to claim 1, wherein $R_4$ represents a hydrogen atom or a $C_{1-3}$ alkyl group.
7. The derivative according to claim 1, wherein $R_3$ represents a hydrogen atom or a methyl group.
8. The derivative according to claim 1, wherein the derivative is:
  1-((6-chloropyridin-3-yl)methyl)-8-nitro-1,2,3,5,6,7-hexahydro imidazo[1,2-a]pyridin-5-ol;
  1-((6-chloropyridin-3-yl)methyl)-5-methoxy-8-nitro-1,2,3,5,6,7-hexahydroimidazo[1,2-a]pyridine;
  1-((6-chloropyridin-3-yl)methyl)-5-ethoxy-8-nitro-1,2,3,5,6,7-hexahydroimidazor[1,2-a]pyridine;
  1-((6-chloropyridin-3-yl)methyl)-5-propoxy-8-nitro-1,2,3,5,6,7-hexahydroimidazo[1,2-a]pyridine;
  1-((6-chloropyridin-3-yl)methyl)-5-isopropoxy-8-nitro-1,2,3,5,6,7-hexahydroimidazo[1,2-a]pyridine;
  1-((6-chloropyridin-3-yl)methyl)-8-nitro-5-pentyloxy-1,2,3,5,6,7-hexahydroimidazo[1,2-a]pyridine;
  5-(2-chloroethoxy)-1-((6-chloropyridin-3-yl)methyl)-8-nitro-1,2,3,5,6,7-hexahydroimidazo[1,2-a]pyridine;
  1-((6-chloropyridin-3-yl)methyl)-9-nitro-2,3,4,6,7,8-hexahydro-1H-pyrido[1,2-a]pyrimidin-6-ol;
  1-((2-chlorothiazol-5-yl)methyl)-8-nitro-1,2,3,5,6,7-hexahydro imidazo[1,2-a]pyridin-5-ol;
  1-((2-chlorothiazolyl-5-yl)methyl)-5-ethoxy-8-nitro-1,2,3,5,6,7-hexahydroimidazor[1,2-a]pyridine;
  8-nitro-1-((tetrahydrofuran-3-yl)methyl)-1,2,3,5,6,7-hexahydro imidazo[1,2-a]pyridin-5-ol;
  8-nitro-5-propoxy-1-((tetrahvdrofuran-3-yl)methyl)-1,2,3,5,6,7-hexahydroimidazo[1,2-a]pyridine;
  1-((6-chloropyridin-3-yl)methyl)-8-nitro-1,2,3,5,6,7-hexahydro imidazo[1,2-a]pyridin-5-yl acetate;
  1-((6-chloropyridin-3-yl)methyl)-5-(ethylthio)-8-nitro-1,2,3,5,6,7-hexahydroimidazo[1,2-a]pyridine;
  (E)-1-((6-chloropyridin-3-yl)methyl)-8-nitro-2,3,6,7-tetrahydro imidazo[1,2-a]pyridin -5(1H)-one oxime; or
  (E)-1-((6-chloropyridin-3-yl)methyl)-8-nitro-2,3,6.7-tetrahydro imidazo[1,2-a]pyridin -5(1H)-one O-methyl oxime.
9. A method for preparing an insecticidal composition comprising mixing the derivative or the agriculturally acceptable salt thereof according to claim 1 with an agriculturally acceptable carrier or diluent, thereby forming the insecticidal composition.
10. An insecticidal composition comprising an effective amount of a derivative according to claim 1 or an agriculturally acceptable salt thereof in mixture with an agriculturally acceptable carrier or diluent.

* * * * *